US007754449B2

(12) United States Patent
Neefe et al.

(10) Patent No.: US 7,754,449 B2
(45) Date of Patent: Jul. 13, 2010

(54) HUMAN PAPILLOMA VIRUS TREATMENT

(75) Inventors: John R. Neefe, Devon, PA (US); Stephen E. Goldstone, New York, NY (US); Mark T. Winnett, Phoenixville, PA (US); Marvin Siegel, Blue Bell, PA (US); Leslie J. Boux, Victoria (CA)

(73) Assignee: Nventa Biopharmaceuticals Corporation, La Jolla, CA (US)

( * ) Notice: Subject to any disclaimer, the term of this patent is extended or adjusted under 35 U.S.C. 154(b) by 0 days.

(21) Appl. No.: 11/796,144

(22) Filed: Apr. 26, 2007

(65) Prior Publication Data

US 2008/0063661 A1    Mar. 13, 2008

Related U.S. Application Data

(60) Division of application No. 10/871,138, filed on Jun. 18, 2004, now Pat. No. 7,211,411, which is a continuation of application No. 10/365,908, filed on Feb. 13, 2003, now Pat. No. 6,797,491, which is a division of application No. 09/891,823, filed on Jun. 26, 2001, now abandoned.

(60) Provisional application No. 60/214,202, filed on Jun. 26, 2000.

(51) Int. Cl.
C12P 21/06        (2006.01)
(52) U.S. Cl. .................................................. 435/69.1
(58) Field of Classification Search ................ 435/69.1, 435/69.7
See application file for complete search history.

(56) References Cited

U.S. PATENT DOCUMENTS

| 4,666,847 A | 5/1987 | Alford et al. | |
| 4,716,038 A | 12/1987 | Stanford et al. | 424/92 |
| 4,724,144 A | 2/1988 | Rook et al. | 424/93 |
| 4,734,362 A | 3/1988 | Hung et al. | |
| 4,784,941 A | 11/1988 | Watanabe et al. | |
| 4,797,359 A | 1/1989 | Finkelstein et al. | |
| 4,918,164 A | 4/1990 | Hellstrom et al. | |
| 4,918,166 A | 4/1990 | Kingsman et al. | 530/350 |
| 5,114,844 A | 5/1992 | Cohen et al. | 435/7 |
| 5,204,259 A | 4/1993 | Helting et al. | |
| 5,256,767 A | 10/1993 | Salk et al. | |
| 5,348,945 A | 9/1994 | Berberian et al. | 514/21 |
| 5,504,005 A | 4/1996 | Bloom et al. | 435/253 |
| 5,578,300 A | 11/1996 | Schmidt et al. | 424/78.08 |
| 5,580,563 A | 12/1996 | Tam | 424/197 |
| 5,599,545 A | 2/1997 | Stanford et al. | 424/282.1 |
| 5,736,146 A | 4/1998 | Cohen et al. | 424/197.11 |
| 5,750,119 A | 5/1998 | Srivastava | 424/277.1 |
| 5,830,464 A | 11/1998 | Srivastava | 424/93.71 |
| 5,837,251 A | 11/1998 | Srivastava | 424/193.1 |
| 5,858,368 A | 1/1999 | Smith et al. | 424/192.1 |
| 5,925,362 A | 7/1999 | Spitler et al. | |
| 5,935,576 A | 8/1999 | Srivastava | 424/184.1 |
| 5,948,646 A | 9/1999 | Srivastava | 435/69.3 |
| 5,961,979 A | 10/1999 | Srivastava | 424/193.1 |
| 5,985,270 A | 11/1999 | Srivastava | 424/93.71 |
| 5,997,873 A | 12/1999 | Srivastava | 424/193.1 |
| 6,007,806 A | 12/1999 | Lathe et al. | 424/93.2 |
| 6,007,821 A | 12/1999 | Srivastava et al. | 424/193.1 |
| 6,017,540 A | 1/2000 | Srivastava et al. | 424/193.1 |
| 6,017,544 A | 1/2000 | Srivastava | 424/277.1 |
| 6,030,618 A | 2/2000 | Srivastava | 424/184.1 |
| 6,048,530 A | 4/2000 | Srivastava | 424/193.1 |
| 6,130,087 A | 10/2000 | Srivastava et al. | 435/372.3 |
| 6,136,315 A | 10/2000 | Srivastava | 424/193.1 |
| 6,139,841 A | 10/2000 | Srivastava | 424/193.1 |
| 6,143,299 A | 11/2000 | Srivastava | 424/193.1 |
| 6,156,302 A | 12/2000 | Srivastava | 424/93.1 |
| 6,162,436 A | 12/2000 | Srivastava | 424/193.1 |
| 6,168,793 B1 | 1/2001 | Srivastava | 424/193.1 |
| 6,187,312 B1 | 2/2001 | Srivastava | 424/193.1 |
| 6,322,790 B1 | 11/2001 | Srivastava | 424/193.1 |
| 6,335,183 B1 | 1/2002 | Young et al. | 435/69.7 |

(Continued)

FOREIGN PATENT DOCUMENTS

CN        1248631 A        3/2000

(Continued)

OTHER PUBLICATIONS

Agranovsky et ak., "Putative 65 kDa Protein of Beet Yellows Closterovirus Is a Homologue of HSP70 Heat Shock Proteins," J. Mol. Biol., 217:603-610 (1991).

(Continued)

Primary Examiner—Ali R. Salimi
(74) Attorney, Agent, or Firm—Sughrue Mion, PLLC

(57) ABSTRACT

Disclosed is a method of treating a wart in a subject by administering to the subject a composition containing (1) a heat shock protein or an immunostimulatory fragment thereof, and (2) a protein of a human papilloma virus or an antigenic fragment thereof. Also disclosed is a method of treating a human papilloma virus infection in a subject infected or suspected of being infected with a human papilloma virus of a first type by administering to the subject a composition containing (1) a heat shock protein or an antigenic fragment thereof, and (2) a protein of a human papilloma virus of a second type or an antigenic fragment thereof, where the first type and second type are different.

25 Claims, No Drawings

U.S. PATENT DOCUMENTS

| | | | |
|---|---|---|---|
| 6,338,952 B1 | 1/2002 | Young et al. | 435/69.7 |
| 6,380,157 B1 | 4/2002 | Jarrett et al. | |
| 6,495,347 B1 | 12/2002 | Siegel et al. | 435/69.7 |
| 6,497,880 B1 | 12/2002 | Wisniewski | 424/190.1 |
| 6,524,825 B1 | 2/2003 | Mizzen et al. | 435/69.7 |
| 7,211,411 B2 * | 5/2007 | Neefe et al. | 435/69.1 |

FOREIGN PATENT DOCUMENTS

| | | |
|---|---|---|
| EP | 0 118 393 | 9/1984 |
| EP | 0 230 222 | 9/1987 |
| EP | 0 262 710 | 4/1988 |
| EP | 0 322 990 | 7/1989 |
| EP | 0 521 220 | 1/1993 |
| GB | 2 251 186 | 7/1992 |
| WO | WO 85/05034 | 11/1985 |
| WO | WO 88/00974 | 2/1988 |
| WO | WO 88/05823 | 8/1988 |
| WO | WO 88/06591 | 9/1988 |
| WO | WO 89/12455 | 12/1989 |
| WO | WO90/10230 | 9/1990 |
| WO | WO 90/15873 | 12/1990 |
| WO | WO 91/02542 | 3/1991 |
| WO | WO 91/15572 | 10/1991 |
| WO | WO 92/08484 | 5/1992 |
| WO | WO 92/08488 | 5/1992 |
| WO | WO 93/17712 | 9/1993 |
| WO | WO 94/03208 | 2/1994 |
| WO | WO 94/29459 | 12/1994 |
| WO | WO 95/24923 | 9/1995 |
| WO | WO 95/31994 | 11/1995 |
| WO | WO 96/10421 | 4/1996 |
| WO | WO 96/19496 | 6/1996 |
| WO | WO 96/26277 | 8/1996 |
| WO | WO 97/06821 | 2/1997 |
| WO | WO 97/26910 | 7/1997 |
| WO | WO 98/04706 | 2/1998 |
| WO | WO 98/23735 | 6/1998 |
| WO | WO 98/35705 | 8/1998 |
| WO | WO 99/07860 | 2/1999 |
| WO | WO 99/33868 | 7/1999 |
| WO | WO 00/19828 | 4/2000 |
| WO | WO 00/23093 | 4/2000 |
| WO | WO 01/04344 | 1/2001 |
| WO | WO 01/17554 | 3/2001 |
| WO | WO 01/52791 | 7/2001 |
| WO | WO 01/52877 | 7/2001 |
| WO | WO 01/52890 | 7/2001 |
| WO | WO 01/53457 | 7/2001 |

OTHER PUBLICATIONS

Aldovini et al., Nature, vol. 351 No. 6326, pp. 479-482 (Jun. 1991).
Anthony et al., "Priming of CD8+ CTL Effector Cells In Mice By Immunization With a Stress Protein-Influenza Virus Nucleoprotein Fusion Molecule" Vaccine, 17:373-383 (1999).
Ardeshir et al., "A 75 Kd Merozoite Surface Protein of Plasmodium Falciparum which is Related to the 70 kd Heat-Shock Proteins," EMBO J., 6(2):493-499 (1987).
Arnosti et al., "Characterization of heat shock in Bacillus subtilis ," J. Bact., 168(3):1243-1249 (Dec. 1986).
Arrigo and Welch, "Characterization and Purification of the Small 28,000-Dalton Mammalian Heat Shock Protein", J. Biol. Chem., 262(32):15359-15369 (1987).
Bardwell et al., Journal of Biological Chemistry, vol. 261 No. 4, pp. 1782-1785 (Feb. 1986).
Barrios et al., "Heat shock proteins as carrier molecules: in vivo helper effect mediated by Escherichia coli GroEL and DnaK proteins requires cross-linking with antigen," Clin. Exp. Immunol., 98:229-233 (1994).
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guerin priming," Eur. J. Immunol., 22:1365-1372 (1992).
Beech et al., "CD4+ Th2 cells specific for mycobacterial 65-kilodalton heat shock protein protect against pristane-induced arthritis," J. Immunol. 159:3692-3697 (1997).
Bennett et al., "Help for Cytotoxic-T-cell Responses is Mediated by CD40 Signalling," Nature 393:478-480 (Jun. 4, 1998).
Bertelli et al., "BCG-Induced Resistance in Trypanosoma cruzi Experimental Infections," Tropenmed Parasitol, 32:93-96 (1981).
Birk et al., "T-cell autoimmunity in type 1 diabetes mellitus," Curr. Opin. Immunol., 5:903-909 (1993).
Blachere et al., "Heat Shock Protein-Peptide Complexes, Reconstituted in Vitro, Elicit Peptide-specific Cytotoxic T Lymphocyte Response and Tumor Immunity," J. Exp. Med. 186(8):1315-1322 (Oct. 20, 1997).
Blachere et al., Journal of Immunology, vol. 14, pp. 352-356 (1993).
Blander and Horwitz, "Major Cytoplasmic Membrane Protein of Legionella Pneumophila, a Genus Common Antigen and Member of the hsp 60 Family of Heat Shock Proteins, Induces Protective Immunity in a Guinea Pig Model of Legionnaires' Disease," J. Clin. Invest., 91:717-723 (1993).
Borysiewicz et al, "A recombinant vaccinia virus encoding human papillomavirus types 16 and 18, E6 and E7 proteins as immunotherapy for cervical cancer," Lancet, 347:1523-27 (1996).
Breloer et al., "In Vivo and In Vitro Activation of T Cells After Administration of Ag-Negative Heat Shock Proteins," J. Of Immun. 162:3141-3147 (1999).
Britton et al., Leprosy Review, vol. 57 Supp. 2, pp. 67-75 (1986).
Butini et al., "Comparative Analysis of HIV-specific CTL Activity in Lymphoid Tissue and Peripheral Blood," J. Cell Biochem. Suppl. 18B Abstract J306 (1994).
Cain and Howett, "Preventing cervical cancer," Science, 288:1753-54 (2000).
Cassell et al., "A Phase II Study on the Postsurgical Management of Stage Malignant Melanoma With a Newcastle Disease Virus Oncolysate," Cancer, 52:856-860 (Sep. 1983).
Cassell et al., "Viral Oncolysate in the Management of Malignant Melanoma, I. Preparation of the Oncolysate and Measurement of Immunologic Responses" Cancer, 40:672-679 (Aug. 1977).
Catelli et al., "The common 90-kd protein component of non-transformed '8S' steroid receptors is a heat-shock protein", EMBO J., 4(12):3131-3135 (1985).
Chandrasekhar et al., "Purification and Properties of the groES Morphogenetic Protein of Escherichia coli", J. Biol. Chem., 261(26):12414-12419 (1986).
Chen et al., "Enhancement of DNA vaccine potency by linkage of antigen gene to an HSP70 gene," Cancer Research, 60:1035-1042 (2000).
Chen et al., "Human 60-kDa Heat-Shock Protein: A Danger Signal to the Innate Immune System," J. Of Immunol. 162:3212-3219 (1999).
Chu et al., "Cancer Immunotherapy Using Adjuvant-free, Fusion Protein Encoding M. bovis BCG HSP65 and HPV16 E7", FASEB Journal, 12(5):A909 (Mar. 20, 1998).
Chu et al., "Immunotherapy of a Human Papillomavirus (HPV) Type 16 E7-Expressing Tumour By Administration of Fusion Protein Comprising Mycobacterium bovis Bacille Calmette-Guérin (BCG) hsp65 and HPV16 E7", Clin. Exp. Immunol., 121:216-225 (2000).
Cohen et al., "Immunity to 60 kDa heat shock protein in autoimmune diabetes," Diab. Nutr. Metab., 9(4):229-232 (1996).
Cohen, "Jitters jeopardize AIDS vaccine trials," Science, 262: 980-981 (1993).
Cox et al., Eur. J. Immunol., vol. 18, pp. 2015-2019 (1988).
Dahlseid et al., "PBP74, a new member of the mammalian 70-kDa heat shock protein family, is a mitochondrial protein," Mol Biol Cell. 5(11):1265-1275 (1994).
Davis et al., Gene, vol. 21 No. 3, pages 273-274 (Mar. 1983).
de Gruijl et al., "T cell proliferative responses against human papillomavirus type 16 E7 oncoprotein are most prominent in cervial intraepithelial neoplasia patients with a persistent viral infection," Journal of General Virology, 77:2183-2191 (1996).

De Velasco et al., "Synthetic Peptides Representing T-Cell Epitopes Act as Carriers in Pneumococcal Polysaccharide Conjugate Vaccines," Infect. & Immun., 63:961-968 (1995).
Del Guidice, "Hsp70: a carrier molecule with built-in adjuvanticity," Experientia, 50:1061-1066 (1994).
Del Guidice et al., "Heat shock proteins as "super"-carriers for sporozoite peptide vaccines?", Research In Immunol., 162:703-707 (1991).
Del Guidice et al., "Priming to Heat Shock Proteins in Infants Vaccinated against Pertussis," J. Immunol., 150(5):2025-2032 (1993).
DeNagel et al., "Heat shock proteins in Immune Responses," Crit. Rev. Immunol., 13(1):71-81 (1993).
Doherty et al., Evasion of host immune responses by tumours and viruses, "Vaccines against virally induced cancers," Wiley, Chicester (Ciba Foundation Symposium 187), pp. 245-260. See p. 245, Abstract.
DuBois et al., "Isolation of a Tumor-Associated Transplantation Antigen (TATA) From an SV40-Induced Sarcoma. Resemblance to the TATA of Chemically Induced Neoplasms," Int. J. Cancer, 34:561-566 (1984).
Dubois et al., "Protective immunization of the squirrel monkey against asexual blood stages of *Plasmodium falciparum* by use of parasite protein fractions," Proc. Natl. Acad. Sci., 81:229-232 (1984).
Elias et al., "Induction and therapy of autoimmune diabetes in the non-obese diabetic (NOD/Lt) mouse by a 65-kDa heat shock protein," Proc. Natl. Acad. Sci. USA, 87:1576-1580 (1990).
Engel et al., Biomed. Biochim. Acta, vol. 9, pp. 1065-1071 (1991).
Falk et al., "Cell Mediated Immunity to Human Tumors," Arch. Surg., 107:261-265 (Aug. 1973).
Farrelly et al., Journal of Biological Chemistry, vol. 259 No. 9, pp. 5745-5751 (May 1984).
Ferrero et al., "The GroES homolog of *Helicobacter pylori* confers protective immunity against mucosal infection in mice," Proc. Natl. Acad. Sci. USA, 92:6499-6503 (1995).
Flaherty et al., "Three-dimensional Structure of the ATPase Fragment of a 70K Heat-Shock Cognate Protein," Nature 346:623-628.
Fox, "No Winners Against AIDS", Biotechnology, 12:128 (1994).
Friedland et al., "Mycobacterial 65-kD heat shock protein induces release of proinflammatory cytokines from human monocytic cells," Clin. Exp. Immunol., 91:58-62 (1993).
Galloway, "Papillomavirus oncoproteins as vaccine candidates," Lancet, 347:1498-99 (1996).
Garsia et al., Infection and Immunity, vol. 57 No. 1, pp. 204-12 (Jan. 1989).
Giudice et al., Research in Immunology, vol. 142 No. 8, pp. 703-707 (Oct. 1991).
Goldstone et al., "Activity of HspE7, A Novel Immunotherapy, In Patients With Anogenital Warts", Dis. Colon Rectum, 45:502-507 (2002).
Gomes et al., "Heat shock protein synthesis during development in Caulobacter crescentus," J. Bact., 168(2):923-930 (Nov. 1986).
Gomez et al., "Vaccination with Recombinant Heat Shock Protein 60 from *Histoplasma capsulatum* Protects Mice against Pulmonary Histoplasmosis," Infect. & Immun., 63:2587-2595 (1995).
Gomez et al., Infection and Immunity, vol. 60 No. 7, pp. 2565-2571 (Jul. 1992).
Haanen et al., "Selection of a human T helper type 1-like T cell subset by mycobacteria," J. Exp. Med., 174:583-592 (1991).
Haghbin et al., "Immunotherapy with Oral BCG and Serial Immune Evaluation in Childhood Lymphoblastic Leukemia Following Three Years of Chemotherapy," Cancer, 46:2577-2586 (Dec. 1980).
Hastie et al., "HSP27 Elevated in Mild Allergic Inflammation Protects Airway Epithelium from H2SO4 Effects," Am J. Physiol., 273 (Lung Cell. Mol. Physiol., 17):L401-L409 (1997).
Haynes, "Scientific and Social Issues of Human Immunodeficiency Virus Vaccine Development", Science, 260:1279-1286 (1993).
Huang et al., "In Vivo Cytotoxic T Lymphocyte Elicitation by Mycobacterial Heat Shock Protein 70 Fusion Proteins Maps to a Discrete Domain and Is CD4 T Cell Independent," J. Exp. Med. 191(2):403-408 (Jan. 17, 2000).
Hudson et al., "Active Specific Immunotherapy for Ovarian Cancer," The Lancet, 2:877-879 (Oct. 23, 1976).

Hughes et al., "A Study in Clinical Cancer Immunotherapy," Cancer, 26:269-278 (Aug. 1970).
Humphrey et al., "Adjuvant Immunotherapy for Melanoma," J. of Sur. Oncol., 25:303-305 (1984).
Hunt and Calderwood, "Characterization and Sequence of a Mouse hsp70 Gene and Its Expression in Mouse Cell Lines," Gene 87:199-204 (1990).
Husson and Young, "Genes for the major protein antigens of Mycobacterium tuberculosis: The etiologic agents of tuberculosis and leprosy share an immunodominant antigen," Proc. Natl. Acad. Sci. USA, 84:1679-1683 (1987).
Huygen et al., "Spleen cell cytokine secretion in Mycobacterium bovis BCG-infected mice," Infection and Immunity, 60(7):2880-2886 (1992).
Jacquier-Sarlin, "Protective effects of hsp70 in inflammation," Experientia, 50(11-12):1031-1038 (1994).
Jacobs et al., Nature, vol. 327 No. 6122, pp. 532-535 (Jun. 1987).
Jarecki-Black et al., "The Effect of BCG-Vaccine Upon Experimental Visceral Leishmaniasis in Hampsters," Ann. Clin. Lab. Sci., 14:464-466 (1984).
Jindal, "Heat Shock Proteins: Applications in health and disease," Trends in Biotech, 14(1):17-20, 1996.
Jondal et al., "MHC Class I-Restricted CTL Responses to Exogenous Antigens," Immunity 5:295-203 (Oct. 1996).
Kaufmann et al., "Enumeration of T cells reactive with Mycobacterium tuberculosis organisms and specific for the recombinant mycobacterial 64-kDa protein", Eur. J. Immunol., 17:351-357 (1987).
Kaufmann et al., "Heat-shock protein 60: implications for pathogenesis of and protection against bacterial infections," Immunological Reviews, 121:67-90 (1991).
Kawana et al., "Common Neutralization Epitope In Minor Capsid Protein L2 of Human Papillomavirus types 16 and 6", J. Of Virology, 73:6188-6190 (1999).
Kiessling et al., "Role of hsp60 during autoimmune and bacterial inflammation," Immunological Reviews, 121:91-111 (1991).
Kimmig and Wenk, "Suppression of Parasitaemia from *Litomosoides carinii* by Immunisation with BCG and Microfilariae," Z. Parasitenkd, 67:317-327 (1982).
Kol et al., "Chlamydial and Human Heat Shock Protein 60s Activate Human Vascular Endothelium, Smooth Muscle Cells, and Macrophages," J. Clin. Invest. 103:571-577 (1999).
Konen-Waisman et al., "Self and Foreign 60-Kilodalton Heath Shock Protein T Cell Epitope Peptides Serve As Immunogenic Carriers for a T Cell-Independent Sugar Antigen," Journ. Immunol., 154:5977-5985 (1995).
Konen-Waisman et al., "Self Heat-Shock Protein (hsp60) Peptide Serves in a Conuugate Vaccine against a Lethal Pneumococcal Infection," J. Infect. Diseases 179:403-413 (1999).
La Thangue and Latchman, "A Cellular Protein Related to Heat-Shocked Protein 90 Accumulates during Herpes Simplex Virus Infection and Is Overexpressed in Transformed Cells," Experimental Cell Research, 178:169-179 (1988).
Lamb et al., "Stress Proteins may Provide a Link Between the Immune Response to Infection and Autoimmunity", Intl. Immun., 1(2):191-196 (1989).
Layton et al., Induction of HIV-Specific Cytotoxic T lymphocytes In Vivo with Hybrid HIV-1 V3:Ty-Virus-Like-Particles, J. Immunology, 151(2):1097-1107 (Jul. 1993).
Leung et al., "The immunobiology of heat shock proteins," J. Investig. Allergol. Clin. Immunol., 1(1):23-30, (1991).
Levi et al., "Synthetic recombinant influenza vaccine induces efficient long-term immunity and cross-strain protection," Vaccine, 14:85-92 (1996).
Li and Srivastava, "Tumor Rejection Antigen gp96/grp94 is an ATPase: Implications for Protein Folding and Antigen Presentation," The EMBO Journal, 12(8):3143-3151 (1993).
Lin et al., "Progression from papilloma to carcinoma is accompanied by changes in antibody response to papillomavirus proteins," J. Virol., 67(1):382-389 (1993).
Lindquist, Annual Review of Biochemistry, vol. 55, pp. 1151-1191 (Jul. 1986).

Lindquist and Craig, "The Heat-Shock Proteins," Annu. Rev. Genet., 22:631-677 (1988).

Liu et al., "Recombinant adeno-associated virus expressing human papillomavirus type 16 E7 peptide DNA fused with heat shock protein DNA as a potential vaccine for cervical cancer," J. Virol., 74(6)2888-2894 (2000).

Lussow et al., "Mycobacterial heat-shocked proteins as carrier molecules," Eur. J. Immunol, 21:2297-2302 (1991).

Maytin, "Heat shock proteins and molecular chaperones: implications for adaptive responses in the skin," J. Invest. Dermatol., 104:448-455 (1995).

McCulloch et al., "Recurrent Malignant Melanoma: Effect of Adjuvant Immunotherapy on Survival," Can. Med. Assoc. J., 117:33-36 (Jul. 1977).

McKenzie et al., Journal of Immunology, vol. 147 No. 1, pp. 312-319 (Jul. 1991).

Miller et al., "Immunotherapy in autoimmune diseases," Curr. Opinion In Immun., 3:936-940 (1991).

Minowada et al., "Clinical implications of the stress response," J. Clin. Invest., 95:3-12 (1995).

Moré et al., Activation of cytotoxic T cells in vitro by recombinant gp96 fusion proteins irrespective of the 'fused' antigenic peptide sequence, Immunology Letters, 69:275-282 (1999).

Moser et al., Parasite Immunology, vol. 12, pp. 341-352 (1990).

Motal, "Glycosylphosphatidylinositol-linked Db does not induce an influenza-specific cytotoxic T lymphocyte response or recycle membrane-bound peptides," Eur. J. Immunol., 25:1121-1124 (1995).

Murphy and Lefford, "Host Defenses in Murine Malaria: Induction of a Protracted State of Immunity with a Formalin-Killed Plasmodium berghei Blood Parasite Vaccine," Infec. Immun., 22:798-803 (1978).

Murray et al., "Viral Oncolysate in the Management of Malignant Melanoma, II. Clinical Studies" Cancer, 40:680-686 (Aug. 1977).

Nadler et al., "Interaction of the Immunosupressant Deoxyspergualin with a Member of the Hsp70 Family of Heat Shock Proteins," Science, 258:484-486 (1992).

Nair et al., "Calreticulin Displays in Vivo Peptide-Binding Activity and Can Elicit CTL Responses Against Bound Peptides," J. Immun. 162:6426-6432 (1999).

NCBI Accession CAD93221, Probable Chaperone protein DNAK . . . , Apr. 2005.

NCBI Accession NP_854111, 60 KDA Chaperonin, Apr. 2005.

Noll and Autenrieti, "Immunity against Yersinia enterocolitica by Vaccination with Yersinia HSP60 Immunostimulating Complexes or Yersinia HSP60 plus Interleukin-12", Infect. & Immun., 64:2955-2961 (1996).

Oettgen and Old, "Chapter 6: The History of Cancer Immunotherapy." In Biologic Therapy of Cancer, De Vita, V.T., Hellman, S. and Rosenberg, S.A., eds., (London: J.B. Lippincott) pp. 98-103 (1991).

Orme et al., "Cytokine secretion by CD4 T lymphocytes acquired in response to Mycobacterium tuberculosis infection," J. Immunol., 151(1):518-525 (1993).

Palladino et al., "Expression of a Shared Tumor-Specific Antigen by Two Chemically Induced BALB/c Sarcomas," Cancer Research, 47:5074-5079 (Oct. 1987).

Peetermans et al., "Mycobacterial heat-shock protein 65 induces proinflammatory cytokines but does not activate human mononuclear phagocytes," Scan. J. Immunol., 39:613-617 (1994).

Pinskey et al., "Intravesical Administration of Bacillus Calmette-Guerin in Patients with Recurrent Superficial Carcinoma of the Urinary Bladder: Report of a Prospective, Randomized Trail," Cancer Treat. Rep., 69:47-53 (Jan. 1985).

Polla et al., "Heat shock proteins and inflammation," Current Topics in Microbiology and Immunology, 167:93-105 (1991).

Polla et al., "Regulation and functions of stress proteins in allergy and inflammation," Clinical and Experimental Allergy, 23:548-556 (1993).

Polla et al., "Spontaneous heat shock protein synthesis by alveolar macrophages in interstitial lung disease associated with phagocytosis of eosinophils," Eur. Respir. J., 6:483-488 (1993).

Rico et al., "Characterization of the Immunostimulatory Properties of Leishmania infantum HSP70 by Fusion to the Escherichia coli Maltose-Binding Protein in Normal nu/nu BALB/c Mice," Infection and Immunity 66:347-352 (Jan. 1998).

Roden et al., "Minor Capsid Protein Of Human Genital Papillomaviruses Contains Subdominant, Cross-Neutralizing Epitopes", Virology, 270:254-257 (2000).

Roman et al., "Synthetic peptides non-covalently bound to bacterial hsp 70 elicit peptide-specific T-cell responses in vivo," Immunology, 88(4):487-492 (1992).

Sakai et al., Journal of Biological Chemistry, vol. 260 No. 5, pp. 5055-5060 (Apr. 1985).

Salgaller et al., Cancer Research, vol. 53 No. 9, pp. 2154-2161 (May 1993).

Schild et al., "Stress Proteins and Immunity Mediated by Cytotoxic T Lymphocytes," Current Opinion in Immun. 11:109-113 (1999).

Schoenberger et al., "T-cell Help for Cytotoxic T Lymphocytes is Mediated by CD40-CD40L Interactions," Nature 393:480-483 (Jun. 4, 1998).

Shinnick et al., "The Etiologic Agents of Leprosy and Tuberculosis Share an Immunoreactive protein Antigen with the Vaccine Strain Mycobacterium bovis BCG", Infect. and Immun., 55(8):1932-1935 (1987).

Shinnick et al., Infection and Immunity, vol. 56 No. 2, pp. 446-451 (Feb. 1988).

Silverstein, "The History of Immunology," in Fundamental Immunology, 2.sup.nd Edition, Paul, W.E., ed., (NY:Raven Press), pp. 21, 23-24 (1989).

Snapper et al., Proceedings of the National Academy of Sciences, USA, vol. 85 No. 18, pp. 6987-6991 (Sep. 1988).

Sparks et al., "Immunology and Adjuvant Chemoimmunotherapy of Breast Cancer," Arch Surg, 111:1057-1062 (Oct. 1976).

Spencer et al., "Nonspecific Protection of Mice against Influenza Virus Infection by Local or Systemic Immunization with Bacille Calmette-Guerin," J. Infect, 171-175 (Aug. 1977).

Spindler et al., Journal of Virology, vol. 49 No. 1, pp. 132-141 (Jan. 1984).

Srivastava and Udono, "Heat Shock Protein-Peptide Complexes in Cancer Immunotherapy," Current Opinion In Immun., 6:728-732 (1994).

Srivastava and Old, "Individually Distinct Transplantation Antigens of Chemically Induced Mouse Tumors," Immunology Today, 9:78-83 (Mar. 1988).

Srivastava and Das, "The Serologically Unique Cell Surface Antigen of Zajdela Ascitic Hepatoma is Also Its Tumor-Associated Transplantation Antigen," Int. J. Cancer, 33:417-422 (1984).

Srivastava and Maki, "Stress-Induced Proteins in Immune Response to Cancer," Curr. Top. of Microbiol. Immunol., 167:109-123 (1991).

Srivastava et al., "Tumor Rejection Antigens of Chemically Induced Sarcomas of Inbred Mice," Proc. Natl. Acad. Sci., USA, 83:3407-3411 (May 1986).

Sturrock et al., "Attempts to Induce Resistance to Schistosoma mansoni and S. haematobium in Kenyan Baboons (Papio anubis) Using Non-Specific Immunostimulants," Parasitology, 90:101-110 (1985).

Suto and Srivastava, "A Mechanism for the Specific Immunogenicity of Heat Shock Protein-Chaperoned Peptides," Science 269:1585-1588 (Sep. 15, 1995).

Suzue and Young, "Adjuvant-Free hsp70 Fusion Protein System Elicits Humoral and Cellular Immune Responses to HIV-1 p. 24," Journal of Immunology, 156:873-879 (1996).

Suzue et al., "Heat Shock Fusion Proteins as Vehicles for Antigen Delivery Into the Major Histocompatibility Complex Class I Presentation Pathway," Proc. Natl. Acad. Sci. USA, 94:13146-13151 (Nov. 1997).

Tao et al., Nature, vol. 362 No. 6422, pp. 755-758 (Apr. 1993).

Thole et al., "Antigenic relatedness of a strongly immunogenic 65 kDA mycobacterial protein antigen with a similarly sized ubiquitous bacterial common antigen", Microbial Pathogenesis, 4:71-83 (1988).

Tamura et al., "Immunotherapy of Tumors with Autologous Tumor-Derived Heat Shock Protein Preparations," Science 278:117-120 (Oct. 3, 1997).

Thole et al., "Characterization, Sequence Determination, and Immunogenicity of a 64-Kilodalton Protein of Mycobacterium bovis BCG Expressed in *Escherichia coli* K-12," Infection & Immunol., 55(6):1466-1475 (1987).

Udono et al., "Cellular Requirements for Tumor-Specific Immunity Elicited by Heat Shock Proteins: Tumor Rejection Antigen gp96 Primes CD8 T Cells in vivo," Proc. Natl. Acad. Sci. USA 91:3077-3081 (Apr. 1994).

Udono and Srivastava, "Heat Shock Protein 70-associated Peptides Elicit Specific Cancer Immunity," J. Exp. Med., 178:1391-1396 (Oct. 1993).

Ullrich et al., "A Mouse Tumor-Specific Transplantation Antigen is a Heat Shock-Related Protein," Proc. Natl. Acad. Sci., USA, 83:3121-3125 (May 1986).

van Eden et al., "Cloning of the mycobacterial epitope recognized by T lymphocytes in adjuvant arthritis", Nature, 331(14):171-173 (1988).

Verdegaal et al., "Heat Shcok Protein 65 Induces CD62e, CD106, and CD54 on Cultured Human Endothelial Cells and Increases Their Adhesiveness for Monocytes and Granulocytes," Jour. Immunol., 157:369-376 (1996).

Vignola et al., "Increased expression of heat protein 70 on airway cells in asthma and chronic bronchitis," Am. J. Respir. Cell Mol. Biol., 13:683-691 (1995).

Vodkin and Williams, "A Heat Shock Operon in *Coxiella burnetii* Produces a Major Antigen Homologous to a Protein in Both Mycobacteria and *Escherichia coli*", J. of Bacteriology, 170(3):I227-1234 (1988).

Voellmy et al. "Isolation and functional analysis of a human 70,000-dalton heat shock protein gene segment," Proc Natl Acad Sci U S A. 82(15):4949-53 (1985).

Welch et al., "Biochemical characterization of the mammalian stress proteins and identification of two stress proteins as glucose- and Ca2+-ionophore-regulated proteins," J. Biol. Chem., 258(11):7102-7111 (1983).

Welch and Feramisco, "Purification of the Major Mammalian Heat Shock Proteins", J. Biol. Chem., 257(24):14949-14959 (1982).

Welch and Feramisco, "Rapid Purification of Mammalian 70,000-Dalton Stress Proteins: Affinity of the Proteins for Nucleotides", Mol. Cell. Biol., 5(6):1229-1237 (1985).

Young et al., "The 65kDa antigen of mycobacteria—a common bacterial protein?", Immunol. Today, 8(7-8):215-219 (1987).

Young et al., "Genes for the major protein antigens of the leprosy parasite mycobacterium leprae," Nature, 316:450-452 (1985).

Young et al., "Stress proteins are immune targets in leprosy and tuberculosis," Proc. Natl. Acad. Sci. USA, 85:4267-4270 (1988).

Young, "Stress Proteins and Immunology," Annu. Rev. Immunol., 8:401-420 (1990).

Zhou, "New Fusion Proteins for Immunotherapy of Venereal Disease and Cancer—Is a Heat Shock Protein of Mycobacterium Bovis", Database WPI, Derwent Publications LTD., XP002154481, (Mar. 29, 2000), Abstract.

Zhu et al., "Structural Analysis of Substrate Binding by the Molecular Chaperone DnaK," Science 272:1606-1614 (Jun. 14, 1996).

Zylicz et al., "The grpE Protein of *Escherichia coli*", J. Biol. Chem., 262(36):17437-17442 (1987).

Zylicz and Georgopoulos, "Purification and Properties of the *Escherichia coli* dnaK Replication Protein", J. Biol. Chem., 259(14):8820-8825 (1984).

* cited by examiner

```
                        SEQUENCE LISTING

<160> NUMBER OF SEQ ID NOS: 140

<210> SEQ ID NO 1
<211> LENGTH: 9
<212> TYPE: PRT
<213> ORGANISM: Human papilloma virus

<400> SEQUENCE: 1

Gln Ala Glu Pro Asp Arg Ala His Tyr
1               5

<210> SEQ ID NO 2
<211> LENGTH: 10
<212> TYPE: PRT
<213> ORGANISM: Human papilloma virus

<400> SEQUENCE: 2

Gln Pro Glu Thr Thr Asp Leu Tyr Cys Tyr
1               5                   10

<210> SEQ ID NO 3
<211> LENGTH: 9
<212> TYPE: PRT
<213> ORGANISM: Human papilloma virus

<400> SEQUENCE: 3

Tyr Met Leu Asp Leu Gln Pro Glu Thr
1               5

<210> SEQ ID NO 4
<211> LENGTH: 9
<212> TYPE: PRT
<213> ORGANISM: Human papilloma virus

<400> SEQUENCE: 4

Thr Leu His Glu Tyr Met Leu Asp Leu
1               5

<210> SEQ ID NO 5
<211> LENGTH: 9
<212> TYPE: PRT
```

```
<213> ORGANISM: Human papilloma virus

<400> SEQUENCE: 5

Leu Leu Met Gly Thr Leu Gly Ile Val
1               5

<210> SEQ ID NO 6
<211> LENGTH: 9
<212> TYPE: PRT
<213> ORGANISM: Human papilloma virus

<400> SEQUENCE: 6

Thr Leu Glu Asp Leu Leu Met Gly Thr
1               5

<210> SEQ ID NO 7
<211> LENGTH: 9
<212> TYPE: PRT
<213> ORGANISM: Human papilloma virus

<400> SEQUENCE: 7

Thr Pro Thr Leu His Glu Tyr Met Leu
1               5

<210> SEQ ID NO 8
<211> LENGTH: 10
<212> TYPE: PRT
<213> ORGANISM: Human papilloma virus

<400> SEQUENCE: 8

Thr Phe Cys Cys Lys Cys Asp Ser Thr Leu
1               5                   10

<210> SEQ ID NO 9
<211> LENGTH: 9
<212> TYPE: PRT
<213> ORGANISM: Human papilloma virus

<400> SEQUENCE: 9

His Tyr Asn Ile Val Thr Phe Cys Cys
1               5

<210> SEQ ID NO 10
<211> LENGTH: 9
<212> TYPE: PRT
<213> ORGANISM: Human papilloma virus

<400> SEQUENCE: 10

Cys Tyr Glu Gln Leu Asn Asp Ser Ser
1               5

<210> SEQ ID NO 11
<211> LENGTH: 10
<212> TYPE: PRT
<213> ORGANISM: Human papilloma virus

<400> SEQUENCE: 11

Asp Thr Pro Thr Leu His Glu Tyr Met Leu
1               5                   10

<210> SEQ ID NO 12
<211> LENGTH: 10
<212> TYPE: PRT
<213> ORGANISM: Human papilloma virus
```

```
<400> SEQUENCE: 12

Gly Ile Val Cys Pro Ile Cys Ser Gln Lys
 1               5                  10

<210> SEQ ID NO 13
<211> LENGTH: 10
<212> TYPE: PRT
<213> ORGANISM: Human papilloma virus

<400> SEQUENCE: 13

Cys Val Gln Ser Thr His Val Asp Ile Arg
 1               5                  10

<210> SEQ ID NO 14
<211> LENGTH: 9
<212> TYPE: PRT
<213> ORGANISM: Human papilloma virus

<400> SEQUENCE: 14

Ile Val Cys Pro Ile Cys Ser Gln Lys
 1               5

<210> SEQ ID NO 15
<211> LENGTH: 9
<212> TYPE: PRT
<213> ORGANISM: Human papilloma virus

<400> SEQUENCE: 15

Val Gln Ser Thr His Val Asp Ile Arg
 1               5

<210> SEQ ID NO 16
<211> LENGTH: 9
<212> TYPE: PRT
<213> ORGANISM: Human papilloma virus

<400> SEQUENCE: 16

Cys Cys Lys Cys Asp Ser Thr Leu Arg
 1               5

<210> SEQ ID NO 17
<211> LENGTH: 10
<212> TYPE: PRT
<213> ORGANISM: Human papilloma virus

<400> SEQUENCE: 17

Leu Arg Leu Cys Val Gln Ser Thr His Val
 1               5                  10

<210> SEQ ID NO 18
<211> LENGTH: 10
<212> TYPE: PRT
<213> ORGANISM: Human papilloma virus

<400> SEQUENCE: 18

Arg Thr Leu Glu Asp Leu Leu Met Gly Thr
 1               5                  10

<210> SEQ ID NO 19
<211> LENGTH: 10
<212> TYPE: PRT
<213> ORGANISM: Human papilloma virus

<400> SEQUENCE: 19
```

```
Asp Glu Ile Asp Gly Pro Ala Gly Gln Ala
1               5                   10

<210> SEQ ID NO 20
<211> LENGTH: 9
<212> TYPE: PRT
<213> ORGANISM: Human papilloma virus

<400> SEQUENCE: 20

Val Asp Ile Arg Thr Leu Glu Asp Leu
1               5

<210> SEQ ID NO 21
<211> LENGTH: 9
<212> TYPE: PRT
<213> ORGANISM: Human papilloma virus

<400> SEQUENCE: 21

Leu Gly Ile Val Cys Pro Ile Cys Ser
1               5

<210> SEQ ID NO 22
<211> LENGTH: 9
<212> TYPE: PRT
<213> ORGANISM: Human papilloma virus

<400> SEQUENCE: 22

Leu Glu Asp Leu Leu Met Gly Thr Leu
1               5

<210> SEQ ID NO 23
<211> LENGTH: 9
<212> TYPE: PRT
<213> ORGANISM: Human papilloma virus

<400> SEQUENCE: 23

Thr Asp Leu Tyr Cys Tyr Glu Gln Leu
1               5

<210> SEQ ID NO 24
<211> LENGTH: 9
<212> TYPE: PRT
<213> ORGANISM: Human papilloma virus

<400> SEQUENCE: 24

Glu Glu Asp Glu Ile Asp Gly Pro Ala
1               5

<210> SEQ ID NO 25
<211> LENGTH: 10
<212> TYPE: PRT
<213> ORGANISM: Human papilloma virus

<400> SEQUENCE: 25

Asn Asp Ser Ser Glu Glu Glu Asp Glu Ile
1               5                   10

<210> SEQ ID NO 26
<211> LENGTH: 9
<212> TYPE: PRT
<213> ORGANISM: Human papilloma virus

<400> SEQUENCE: 26

Leu Gln Pro Glu Thr Thr Asp Leu Tyr
1               5
```

```
<210> SEQ ID NO 27
<211> LENGTH: 10
<212> TYPE: PRT
<213> ORGANISM: Human papilloma virus

<400> SEQUENCE: 27

Gly Gln Ala Glu Pro Asp Arg Ala His Tyr
 1               5                  10

<210> SEQ ID NO 28
<211> LENGTH: 9
<212> TYPE: PRT
<213> ORGANISM: Human papilloma virus

<400> SEQUENCE: 28

Asp Ile Arg Thr Leu Glu Asp Leu Leu
 1               5

<210> SEQ ID NO 29
<211> LENGTH: 9
<212> TYPE: PRT
<213> ORGANISM: Human papilloma virus

<400> SEQUENCE: 29

Glu Pro Asp Arg Ala His Tyr Asn Ile
 1               5

<210> SEQ ID NO 30
<211> LENGTH: 10
<212> TYPE: PRT
<213> ORGANISM: Human papilloma virus

<400> SEQUENCE: 30

Cys Cys Lys Cys Asp Ser Thr Leu Arg Leu
 1               5                  10

<210> SEQ ID NO 31
<211> LENGTH: 8
<212> TYPE: PRT
<213> ORGANISM: Human papilloma virus

<400> SEQUENCE: 31

Asp Ile Arg Thr Leu Glu Asp Leu
 1               5

<210> SEQ ID NO 32
<211> LENGTH: 10
<212> TYPE: PRT
<213> ORGANISM: Human papilloma virus

<400> SEQUENCE: 32

Asp Arg Ala His Tyr Asn Ile Val Thr Phe
 1               5                  10

<210> SEQ ID NO 33
<211> LENGTH: 9
<212> TYPE: PRT
<213> ORGANISM: Human papilloma virus

<400> SEQUENCE: 33

Ile Arg Thr Leu Glu Asp Leu Leu Met
 1               5
```

<210> SEQ ID NO 34
<211> LENGTH: 9
<212> TYPE: PRT
<213> ORGANISM: Human papilloma virus

<400> SEQUENCE: 34

Leu Arg Leu Cys Val Gln Ser Thr His
1               5

<210> SEQ ID NO 35
<211> LENGTH: 10
<212> TYPE: PRT
<213> ORGANISM: Human papilloma virus

<400> SEQUENCE: 35

His Gly Asp Thr Pro Thr Leu His Glu Tyr
1               5                   10

<210> SEQ ID NO 36
<211> LENGTH: 10
<212> TYPE: PRT
<213> ORGANISM: Human papilloma virus

<400> SEQUENCE: 36

Glu Pro Asp Arg Ala His Tyr Asn Ile Val
1               5                   10

<210> SEQ ID NO 37
<211> LENGTH: 10
<212> TYPE: PRT
<213> ORGANISM: Human papilloma virus

<400> SEQUENCE: 37

Val Asp Ile Arg Thr Leu Glu Asp Leu Leu
1               5                   10

<210> SEQ ID NO 38
<211> LENGTH: 10
<212> TYPE: PRT
<213> ORGANISM: Human papilloma virus

<400> SEQUENCE: 38

Glu Asp Leu Leu Met Gly Thr Leu Gly Ile
1               5                   10

<210> SEQ ID NO 39
<211> LENGTH: 11
<212> TYPE: PRT
<213> ORGANISM: Human papilloma virus

<400> SEQUENCE: 39

Thr Leu Glu Asp Leu Leu Met Gly Thr Leu
1               5                   10

<210> SEQ ID NO 40
<211> LENGTH: 9
<212> TYPE: PRT
<213> ORGANISM: Human papilloma virus

<400> SEQUENCE: 40

Ala His Tyr Asn Ile Val Thr Phe Cys
1               5

<210> SEQ ID NO 41
<211> LENGTH: 9

<212> TYPE: PRT
<213> ORGANISM: Human papilloma virus

<400> SEQUENCE: 41

Ser Thr His Val Asp Ile Arg Thr Leu
1               5

<210> SEQ ID NO 42
<211> LENGTH: 10
<212> TYPE: PRT
<213> ORGANISM: Human papilloma virus

<400> SEQUENCE: 42

Thr Leu Glu Asp Leu Leu Met Gly Thr Leu
1               5                   10

<210> SEQ ID NO 43
<211> LENGTH: 10
<212> TYPE: PRT
<213> ORGANISM: Human papilloma virus

<400> SEQUENCE: 43

His Val Asp Ile Arg Thr Leu Glu Asp Leu
1               5                   10

<210> SEQ ID NO 44
<211> LENGTH: 9
<212> TYPE: PRT
<213> ORGANISM: Human papilloma virus

<400> SEQUENCE: 44

Cys Lys Cys Asp Ser Thr Leu Arg Leu
1               5

<210> SEQ ID NO 45
<211> LENGTH: 9
<212> TYPE: PRT
<213> ORGANISM: Human papilloma virus

<400> SEQUENCE: 45

Gly Asp Thr Pro Thr Leu His Glu Tyr
1               5

<210> SEQ ID NO 46
<211> LENGTH: 10
<212> TYPE: PRT
<213> ORGANISM: Human papilloma virus

<400> SEQUENCE: 46

Met Gly Thr Leu Gly Ile Val Cys Pro Ile
1               5                   10

<210> SEQ ID NO 47
<211> LENGTH: 10
<212> TYPE: PRT
<213> ORGANISM: Human papilloma virus

<400> SEQUENCE: 47

Asp Leu Leu Met Gly Thr Leu Gly Ile Val
1               5                   10

<210> SEQ ID NO 48
<211> LENGTH: 9
<212> TYPE: PRT
<213> ORGANISM: Human papilloma virus

```
<400> SEQUENCE: 48

Arg Ala His Tyr Asn Ile Val Thr Phe
 1               5

<210> SEQ ID NO 49
<211> LENGTH: 10
<212> TYPE: PRT
<213> ORGANISM: Human papilloma virus

<400> SEQUENCE: 49

Pro Thr Leu His Glu Tyr Met Leu Asp Leu
 1               5                   10

<210> SEQ ID NO 50
<211> LENGTH: 9
<212> TYPE: PRT
<213> ORGANISM: Human papilloma virus

<400> SEQUENCE: 50

Gly Thr Leu Gly Ile Val Cys Pro Ile
 1               5

<210> SEQ ID NO 51
<211> LENGTH: 9
<212> TYPE: PRT
<213> ORGANISM: Human papilloma virus

<400> SEQUENCE: 51

Asp Ser Gln Pro Leu Lys Gln His Tyr
 1               5

<210> SEQ ID NO 52
<211> LENGTH: 10
<212> TYPE: PRT
<213> ORGANISM: Human papilloma virus

<400> SEQUENCE: 52

Pro Pro Asp Pro Val Gly Leu His Cys Tyr
 1               5                   10

<210> SEQ ID NO 53
<211> LENGTH: 9
<212> TYPE: PRT
<213> ORGANISM: Human papilloma virus

<400> SEQUENCE: 53

Thr Leu Lys Asp Ile Val Leu Asp Leu
 1               5

<210> SEQ ID NO 54
<211> LENGTH: 9
<212> TYPE: PRT
<213> ORGANISM: Human papilloma virus

<400> SEQUENCE: 54

Leu Leu Leu Gly Thr Leu Asn Ile Val
 1               5

<210> SEQ ID NO 55
<211> LENGTH: 10
<212> TYPE: PRT
<213> ORGANISM: Human papilloma virus

<400> SEQUENCE: 55
```

```
Gln Leu Val Asp Ser Ser Glu Asp Glu Val
1               5                   10

<210> SEQ ID NO 56
<211> LENGTH: 9
<212> TYPE: PRT
<213> ORGANISM: Human papilloma virus

<400> SEQUENCE: 56

Val Gln Gln Leu Leu Leu Gly Thr Leu
1               5

<210> SEQ ID NO 57
<211> LENGTH: 10
<212> TYPE: PRT
<213> ORGANISM: Human papilloma virus

<400> SEQUENCE: 57

Val Leu Asp Leu Gln Pro Pro Asp Pro Val
1               5                   10

<210> SEQ ID NO 58
<211> LENGTH: 9
<212> TYPE: PRT
<213> ORGANISM: Human papilloma virus

<400> SEQUENCE: 58

His Val Thr Leu Lys Asp Ile Val Leu
1               5

<210> SEQ ID NO 59
<211> LENGTH: 9
<212> TYPE: PRT
<213> ORGANISM: Human papilloma virus

<400> SEQUENCE: 59

His Tyr Gln Ile Val Thr Cys Cys Cys
1               5

<210> SEQ ID NO 60
<211> LENGTH: 9
<212> TYPE: PRT
<213> ORGANISM: Human papilloma virus

<400> SEQUENCE: 60

Cys Tyr Glu Gln Leu Val Asp Ser Ser
1               5

<210> SEQ ID NO 61
<211> LENGTH: 10
<212> TYPE: PRT
<213> ORGANISM: Human papilloma virus

<400> SEQUENCE: 61

Glu Val Asp Gly Gln Asp Ser Gln Pro Leu
1               5                   10

<210> SEQ ID NO 62
<211> LENGTH: 10
<212> TYPE: PRT
<213> ORGANISM: Human papilloma virus

<400> SEQUENCE: 62

Asn Ile Val Cys Pro Ile Cys Ala Pro Lys
```

```
<210> SEQ ID NO 63
<211> LENGTH: 10
<212> TYPE: PRT
<213> ORGANISM: Human papilloma virus

<400> SEQUENCE: 63

Val Val Gln Cys Thr Glu Thr Asp Ile Arg
1               5                   10

<210> SEQ ID NO 64
<211> LENGTH: 9
<212> TYPE: PRT
<213> ORGANISM: Human papilloma virus

<400> SEQUENCE: 64

Ile Val Cys Pro Ile Cys Ala Pro Lys
1               5

<210> SEQ ID NO 65
<211> LENGTH: 9
<212> TYPE: PRT
<213> ORGANISM: Human papilloma virus

<400> SEQUENCE: 65

Val Gln Cys Thr Glu Thr Asp Ile Arg
1               5

<210> SEQ ID NO 66
<211> LENGTH: 9
<212> TYPE: PRT
<213> ORGANISM: Human papilloma virus

<400> SEQUENCE: 66

Cys Cys Gly Cys Asp Ser Asn Val Arg
1               5

<210> SEQ ID NO 67
<211> LENGTH: 9
<212> TYPE: PRT
<213> ORGANISM: Human papilloma virus

<400> SEQUENCE: 67

Val Arg Leu Val Val Gln Cys Thr Glu
1               5

<210> SEQ ID NO 68
<211> LENGTH: 9
<212> TYPE: PRT
<213> ORGANISM: Human papilloma virus

<400> SEQUENCE: 68

Gly Arg His Val Thr Leu Lys Asp Ile
1               5

<210> SEQ ID NO 69
<211> LENGTH: 10
<212> TYPE: PRT
<213> ORGANISM: Human papilloma virus

<400> SEQUENCE: 69

Val Thr Leu Lys Asp Ile Val Leu Asp Leu
1               5                   10
```

<210> SEQ ID NO 70
<211> LENGTH: 9
<212> TYPE: PRT
<213> ORGANISM: Human papilloma virus

<400> SEQUENCE: 70

Ile Arg Glu Val Gln Gln Leu Leu Leu
1               5

<210> SEQ ID NO 71
<211> LENGTH: 9
<212> TYPE: PRT
<213> ORGANISM: Human papilloma virus

<400> SEQUENCE: 71

Asp Glu Val Asp Glu Val Asp Gly Gln
1               5

<210> SEQ ID NO 72
<211> LENGTH: 9
<212> TYPE: PRT
<213> ORGANISM: Human papilloma virus

<400> SEQUENCE: 72

Thr Asp Ile Arg Glu Val Gln Gln Leu
1               5

<210> SEQ ID NO 73
<211> LENGTH: 10
<212> TYPE: PRT
<213> ORGANISM: Human papilloma virus

<400> SEQUENCE: 73

Arg Glu Val Gln Gln Leu Leu Leu Gly Thr
1               5                   10

<210> SEQ ID NO 74
<211> LENGTH: 9
<212> TYPE: PRT
<213> ORGANISM: Human papilloma virus

<400> SEQUENCE: 74

Leu Asn Ile Val Cys Pro Ile Cys Ala
1               5

<210> SEQ ID NO 75
<211> LENGTH: 9
<212> TYPE: PRT
<213> ORGANISM: Human papilloma virus

<400> SEQUENCE: 75

Val Gly Leu His Cys Tyr Glu Gln Leu
1               5

<210> SEQ ID NO 76
<211> LENGTH: 9
<212> TYPE: PRT
<213> ORGANISM: Human papilloma virus

<400> SEQUENCE: 76

Val Asp Gly Gln Asp Ser Gln Pro Leu
1               5

<210> SEQ ID NO 77

```
<211> LENGTH: 8
<212> TYPE: PRT
<213> ORGANISM: Human papilloma virus

<400> SEQUENCE: 77

Asp Glu Val Asp Glu Val Asp Gly
  1               5

<210> SEQ ID NO 78
<211> LENGTH: 8
<212> TYPE: PRT
<213> ORGANISM: Human papilloma virus

<400> SEQUENCE: 78

Ser Glu Asp Glu Val Asp Glu Val
  1               5

<210> SEQ ID NO 79
<211> LENGTH: 8
<212> TYPE: PRT
<213> ORGANISM: Human papilloma virus

<400> SEQUENCE: 79

Thr Glu Thr Asp Ile Arg Glu Val
  1               5

<210> SEQ ID NO 80
<211> LENGTH: 9
<212> TYPE: PRT
<213> ORGANISM: Human papilloma virus

<400> SEQUENCE: 80

Leu Gln Pro Pro Asp Pro Val Gly Leu
  1               5

<210> SEQ ID NO 81
<211> LENGTH: 9
<212> TYPE: PRT
<213> ORGANISM: Human papilloma virus

<400> SEQUENCE: 81

Leu Leu Gly Thr Leu Asn Ile Val Cys
  1               5

<210> SEQ ID NO 82
<211> LENGTH: 9
<212> TYPE: PRT
<213> ORGANISM: Human papilloma virus

<400> SEQUENCE: 82

Asp Ile Arg Glu Val Gln Gln Leu Leu
  1               5

<210> SEQ ID NO 83
<211> LENGTH: 9
<212> TYPE: PRT
<213> ORGANISM: Human papilloma virus

<400> SEQUENCE: 83

Gln Pro Leu Lys Gln His Tyr Gln Ile
  1               5

<210> SEQ ID NO 84
<211> LENGTH: 10
<212> TYPE: PRT
```

-continued

<213> ORGANISM: Human papilloma virus

<400> SEQUENCE: 84

Cys Cys Gly Cys Asp Ser Asn Val Arg Leu
1               5                   10

<210> SEQ ID NO 85
<211> LENGTH: 8
<212> TYPE: PRT
<213> ORGANISM: Human papilloma virus

<400> SEQUENCE: 85

Asp Ile Arg Glu Val Gln Gln Leu
1               5

<210> SEQ ID NO 86
<211> LENGTH: 9
<212> TYPE: PRT
<213> ORGANISM: Human papilloma virus

<400> SEQUENCE: 86

Lys Gln His Tyr Gln Ile Val Thr Cys
1               5

<210> SEQ ID NO 87
<211> LENGTH: 10
<212> TYPE: PRT
<213> ORGANISM: Human papilloma virus

<400> SEQUENCE: 87

Val Arg Leu Val Val Gln Cys Thr Glu Thr
1               5                   10

<210> SEQ ID NO 88
<211> LENGTH: 10
<212> TYPE: PRT
<213> ORGANISM: Human papilloma virus

<400> SEQUENCE: 88

Gly Arg His Val Thr Leu Lys Asp Ile Val
1               5                   10

<210> SEQ ID NO 89
<211> LENGTH: 10
<212> TYPE: PRT
<213> ORGANISM: Human papilloma virus

<400> SEQUENCE: 89

Thr Asp Ile Arg Glu Val Gln Gln Leu Leu
1               5                   10

<210> SEQ ID NO 90
<211> LENGTH: 10
<212> TYPE: PRT
<213> ORGANISM: Human papilloma virus

<400> SEQUENCE: 90

Val Gly Leu His Cys Tyr Glu Gln Leu Val
1               5                   10

<210> SEQ ID NO 91
<211> LENGTH: 10
<212> TYPE: PRT
<213> ORGANISM: Human papilloma virus

<400> SEQUENCE: 91

Gln Gln Leu Leu Leu Gly Thr Leu Asn Ile
 1               5                  10

<210> SEQ ID NO 92
<211> LENGTH: 10
<212> TYPE: PRT
<213> ORGANISM: Human papilloma virus

<400> SEQUENCE: 92

Glu Val Gln Gln Leu Leu Leu Gly Thr Leu
 1               5                  10

<210> SEQ ID NO 93
<211> LENGTH: 9
<212> TYPE: PRT
<213> ORGANISM: Human papilloma virus

<400> SEQUENCE: 93

Gln His Tyr Gln Ile Val Thr Cys Cys
 1               5

<210> SEQ ID NO 94
<211> LENGTH: 10
<212> TYPE: PRT
<213> ORGANISM: Human papilloma virus

<400> SEQUENCE: 94

Arg His Val Thr Leu Lys Asp Ile Val Leu
 1               5                  10

<210> SEQ ID NO 95
<211> LENGTH: 9
<212> TYPE: PRT
<213> ORGANISM: Human papilloma virus

<400> SEQUENCE: 95

Cys Thr Glu Thr Asp Ile Arg Glu Val
 1               5

<210> SEQ ID NO 96
<211> LENGTH: 10
<212> TYPE: PRT
<213> ORGANISM: Human papilloma virus

<400> SEQUENCE: 96

Glu Thr Asp Ile Arg Glu Val Gln Gln Leu
 1               5                  10

<210> SEQ ID NO 97
<211> LENGTH: 9
<212> TYPE: PRT
<213> ORGANISM: Human papilloma virus

<400> SEQUENCE: 97

Cys Gly Cys Asp Ser Asn Val Arg Leu
 1               5

<210> SEQ ID NO 98
<211> LENGTH: 8
<212> TYPE: PRT
<213> ORGANISM: Human papilloma virus

<400> SEQUENCE: 98

Leu Gln Pro Pro Asp Val Gly Leu
1               5

<210> SEQ ID NO 99
<211> LENGTH: 10
<212> TYPE: PRT
<213> ORGANISM: Human papilloma virus

<400> SEQUENCE: 99

Leu Gly Thr Leu Asn Ile Val Cys Pro Ile
1               5                   10

<210> SEQ ID NO 100
<211> LENGTH: 10
<212> TYPE: PRT
<213> ORGANISM: Human papilloma virus

<400> SEQUENCE: 100

Gln Pro Leu Lys Gln His Tyr Gln Ile Val
1               5                   10

<210> SEQ ID NO 101
<211> LENGTH: 10
<212> TYPE: PRT
<213> ORGANISM: Human papilloma virus

<400> SEQUENCE: 101

Gly Cys Asp Ser Asn Val Arg Leu Val Val
1               5                   10

<210> SEQ ID NO 102
<211> LENGTH: 10
<212> TYPE: PRT
<213> ORGANISM: Human papilloma virus

<400> SEQUENCE: 102

Lys Gln His Tyr Gln Ile Val Thr Cys Cys
1               5                   10

<210> SEQ ID NO 103
<211> LENGTH: 9
<212> TYPE: PRT
<213> ORGANISM: Human papilloma virus

<400> SEQUENCE: 103

Gly Thr Leu Asn Ile Val Cys Pro Ile
1               5

<210> SEQ ID NO 104
<211> LENGTH: 10
<212> TYPE: PRT
<213> ORGANISM: Human papilloma virus

<400> SEQUENCE: 104

Gln Pro Pro Asp Pro Val Gly Leu His Cys
1               5                   10

<210> SEQ ID NO 105
<211> LENGTH: 10
<212> TYPE: PRT
<213> ORGANISM: Human papilloma virus

<400> SEQUENCE: 105

Gln Asp Ser Gln Pro Leu Lys Gln His Tyr
1               5                   10

<210> SEQ ID NO 106
<211> LENGTH: 9
<212> TYPE: PRT
<213> ORGANISM: Human papilloma virus

<400> SEQUENCE: 106

Asp Ala Gln Pro Leu Thr Gln His Tyr
 1               5

<210> SEQ ID NO 107
<211> LENGTH: 10
<212> TYPE: PRT
<213> ORGANISM: Human papilloma virus

<400> SEQUENCE: 107

Val Val Glu Cys Thr Asp Gly Asp Ile Arg
 1               5                  10

<210> SEQ ID NO 108
<211> LENGTH: 10
<212> TYPE: PRT
<213> ORGANISM: Human papilloma virus

<400> SEQUENCE: 108

Gln Leu Glu Asp Ser Ser Glu Asp Glu Val
 1               5                  10

<210> SEQ ID NO 109
<211> LENGTH: 9
<212> TYPE: PRT
<213> ORGANISM: Human papilloma virus

<400> SEQUENCE: 109

Gln Leu Gln Asp Leu Leu Leu Gly Thr
 1               5

<210> SEQ ID NO 110
<211> LENGTH: 9
<212> TYPE: PRT
<213> ORGANISM: Human papilloma virus

<400> SEQUENCE: 110

Leu Val Thr Leu Lys Asp Ile Val Leu
 1               5

<210> SEQ ID NO 111
<211> LENGTH: 9
<212> TYPE: PRT
<213> ORGANISM: Human papilloma virus

<400> SEQUENCE: 111

His Tyr Gln Ile Leu Thr Cys Cys Cys
 1               5

<210> SEQ ID NO 112
<211> LENGTH: 9
<212> TYPE: PRT
<213> ORGANISM: Human papilloma virus

<400> SEQUENCE: 112

Cys Tyr Glu Gln Leu Glu Asp Ser Ser
 1               5

```
<210> SEQ ID NO 113
<211> LENGTH: 10
<212> TYPE: PRT
<213> ORGANISM: Human papilloma virus

<400> SEQUENCE: 113

Arg Leu Val Thr Leu Lys Asp Ile Val Leu
1               5                   10

<210> SEQ ID NO 114
<211> LENGTH: 10
<212> TYPE: PRT
<213> ORGANISM: Human papilloma virus

<400> SEQUENCE: 114

Lys Val Asp Lys Gln Asp Ala Gln Pro Leu
1               5                   10

<210> SEQ ID NO 115
<211> LENGTH: 9
<212> TYPE: PRT
<213> ORGANISM: Human papilloma virus

<400> SEQUENCE: 115

Val Arg Leu Val Val Glu Cys Thr Asp
1               5

<210> SEQ ID NO 116
<211> LENGTH: 9
<212> TYPE: PRT
<213> ORGANISM: Human papilloma virus

<400> SEQUENCE: 116

Gly Arg Leu Val Thr Leu Lys Asp Ile
1               5

<210> SEQ ID NO 117
<211> LENGTH: 9
<212> TYPE: PRT
<213> ORGANISM: Human papilloma virus

<400> SEQUENCE: 117

Ile Arg Gln Leu Gln Asp Leu Leu Leu
1               5

<210> SEQ ID NO 118
<211> LENGTH: 9
<212> TYPE: PRT
<213> ORGANISM: Human papilloma virus

<400> SEQUENCE: 118

Asp Glu Val Asp Lys Val Asp Lys Gln
1               5

<210> SEQ ID NO 119
<211> LENGTH: 9
<212> TYPE: PRT
<213> ORGANISM: Human papilloma virus

<400> SEQUENCE: 119

Gly Asp Ile Arg Gln Leu Gln Asp Leu
1               5

<210> SEQ ID NO 120
<211> LENGTH: 9
```

```
<212> TYPE: PRT
<213> ORGANISM: Human papilloma virus

<400> SEQUENCE: 120

Leu Gln Asp Leu Leu Leu Gly Thr Leu
1               5

<210> SEQ ID NO 121
<211> LENGTH: 9
<212> TYPE: PRT
<213> ORGANISM: Human papilloma virus

<400> SEQUENCE: 121

Gly Asp Ile Arg Gln Val Gln Asp Leu
1               5

<210> SEQ ID NO 122
<211> LENGTH: 9
<212> TYPE: PRT
<213> ORGANISM: Human papilloma virus

<400> SEQUENCE: 122

Val Asp Lys Gln Asp Ala Gln Pro Leu
1               5

<210> SEQ ID NO 123
<211> LENGTH: 8
<212> TYPE: PRT
<213> ORGANISM: Human papilloma virus

<400> SEQUENCE: 123

Ser Glu Asp Glu Val Asp Lys Val
1               5

<210> SEQ ID NO 124
<211> LENGTH: 8
<212> TYPE: PRT
<213> ORGANISM: Human papilloma virus

<400> SEQUENCE: 124

Thr Asp Gly Asp Ile Arg Gln Leu
1               5

<210> SEQ ID NO 125
<211> LENGTH: 9
<212> TYPE: PRT
<213> ORGANISM: Human papilloma virus

<400> SEQUENCE: 125

Leu Glu Asp Ser Ser Glu Asp Glu Val
1               5

<210> SEQ ID NO 126
<211> LENGTH: 9
<212> TYPE: PRT
<213> ORGANISM: Human papilloma virus

<400> SEQUENCE: 126

Asp Ile Arg Gln Leu Gln Asp Leu Leu
1               5

<210> SEQ ID NO 127
<211> LENGTH: 10
<212> TYPE: PRT
<213> ORGANISM: Human papilloma virus
```

-continued

```
<400> SEQUENCE: 127

Gln Pro Leu Thr Gln His Tyr Gln Ile Leu
1               5                   10

<210> SEQ ID NO 128
<211> LENGTH: 9
<212> TYPE: PRT
<213> ORGANISM: Human papilloma virus

<400> SEQUENCE: 128

Thr Gln His Tyr Gln Ile Leu Thr Cys
1               5

<210> SEQ ID NO 129
<211> LENGTH: 10
<212> TYPE: PRT
<213> ORGANISM: Human papilloma virus

<400> SEQUENCE: 129

Gly Arg Leu Val Thr Leu Lys Asp Ile Val
1               5                   10

<210> SEQ ID NO 130
<211> LENGTH: 10
<212> TYPE: PRT
<213> ORGANISM: Human papilloma virus

<400> SEQUENCE: 130

Gly Asp Ile Arg Gln Leu Gln Asp Leu Leu
1               5                   10

<210> SEQ ID NO 131
<211> LENGTH: 10
<212> TYPE: PRT
<213> ORGANISM: Human papilloma virus

<400> SEQUENCE: 131

Gln Asp Leu Leu Leu Gly Thr Leu Asn Ile
1               5                   10

<210> SEQ ID NO 132
<211> LENGTH: 9
<212> TYPE: PRT
<213> ORGANISM: Human papilloma virus

<400> SEQUENCE: 132

Gln His Tyr Gln Ile Leu Thr Cys Cys
1               5

<210> SEQ ID NO 133
<211> LENGTH: 9
<212> TYPE: PRT
<213> ORGANISM: Human papilloma virus

<400> SEQUENCE: 133

Cys Thr Asp Gly Asp Ile Arg Gln Leu
1               5

<210> SEQ ID NO 134
<211> LENGTH: 11
<212> TYPE: PRT
<213> ORGANISM: Human papilloma virus

<400> SEQUENCE: 134
```

```
Leu Gln Leu Gln Asp Leu Leu Leu Gly Thr Leu
1               5                   10

<210> SEQ ID NO 135
<211> LENGTH: 9
<212> TYPE: PRT
<213> ORGANISM: Human papilloma virus

<400> SEQUENCE: 135

Gln Pro Leu Thr Gln His Tyr Gln Ile
1               5

<210> SEQ ID NO 136
<211> LENGTH: 10
<212> TYPE: PRT
<213> ORGANISM: Human papilloma virus

<400> SEQUENCE: 136

Leu Thr Gln His Tyr Gln Ile Leu Thr Cys
1               5                   10

<210> SEQ ID NO 137
<211> LENGTH: 10
<212> TYPE: PRT
<213> ORGANISM: Human papilloma virus

<400> SEQUENCE: 137

Arg Gln Leu Gln Asp Leu Leu Leu Gly Thr
1               5                   10

<210> SEQ ID NO 138
<211> LENGTH: 9
<212> TYPE: PRT
<213> ORGANISM: Human papilloma virus

<400> SEQUENCE: 138

Cys Cys Cys Gly Cys Asp Ser Asn Val
1               5

<210> SEQ ID NO 139
<211> LENGTH: 10
<212> TYPE: PRT
<213> ORGANISM: Human papilloma virus

<400> SEQUENCE: 139

Asp Gly Asp Ile Arg Gln Leu Gln Asp Leu
1               5                   10

<210> SEQ ID NO 140
<211> LENGTH: 10
<212> TYPE: PRT
<213> ORGANISM: Human papilloma virus

<400> SEQUENCE: 140

Gln Asp Ala Gln Pro Leu Thr Gln His Tyr
1               5                   10
```

HUMAN PAPILLOMA VIRUS TREATMENT

CROSS REFERENCE TO RELATED APPLICATIONS

This application is a divisional of U.S. Application Ser. No. 10/871,138,filed Jun. 18, 2004 now U.S. Pat. No. 7,211,411, which is a continuation of U.S. application Ser. No. 10/365,908, filed Feb. 13, 2003, now U.S. Pat. No. 6,797,491, which is a divisional of U.S. application Ser. No. 09/891,823, filed Jun. 26, 2001, now abandoned, which claims priority from U.S. Provisional Application No. 60/214,202, filed Jun. 26, 2000 . The content of each of these prior application is incorporated herein by reference in their entirety.

FIELD OF THE INVENTION

The invention relates to therapies for human papilloma virus infections.

BACKGROUND OF THE INVENTION

Infection with human papilloma virus (HPV) is common. HPV can be transmitted sexually, and it is estimated that 20-80% of sexually active adults have been infected. While a majority of infections are asymptomatic, infection can lead to the development of genital warts (which have a prevalence of about 1-5% among adults) and cancer of the anogenital tract. Another type of cancer, cervical cancer, is strongly associated with HPV (Frazer, *Genitourin. Med.* 72:398-403, 1996). HPV types 6, 11, 16, 18, 31, and 33 are often associated with an increased risk of cancer, with types 16 and/or 18 being detected in more than 90% of cervical carcinomas (van Driel et al., *Ann. Med.* 28:471-477, 1996). Types 6 and 11 are also associated with anogenital warts. For reviews of papilloma viruses and their associated pathologies, see Shah et al., "Chapter 66: Papillomaviruses," In: *Virology,* 3rd Edition, Fields et al., Eds., Raven Press, Philadelphia, pp 2077-2109, 1996, and zur Hausen, *J. Natl. Cancer Inst.* 92:690-698, 2000.

There is currently no safe and effective way to treat or prevent warts or the diseases described above by targeting the immune system. Efforts to develop such therapies have been hampered for several reasons, one of which is the dogma that antigens from a single HPV type elicit a limited, type-specific immune response. Consequently, it has been suggested that a cocktail containing antigens from several different HPV types is necessary for a broadly effective HPV therapy (Caine et al., *Science* 288:1753, 2000).

SUMMARY OF THE INVENTION

The present invention is based, in part, on the discovery that a fusion protein containing a protein from one HPV type can be used to treat a disease or condition that is caused by infection with another HPV type. For example, an HPV type 16 antigen, fused to a bacterial heat shock protein (hsp), was effective in treating human anogenital warts caused by HPV types other than type 16 (e.g., HPV types 6 and 11). This result supports two contentions: (1) that warts can be treated with an HPV protein and (2) that therapeutic agents aimed at HPV need not contain protein antigens from different HPV types in order to be broadly effective.

Accordingly, the invention features a method of treating a wart in a subject by administering to the subject a composition containing (1) an hsp, or an immunostimulatory fragment thereof, and (2) an HPV protein (e.g., an antigenic protein such as the E7 protein of, e.g., HPV type 16) or an antigenic fragment thereof. These components may be referred to herein as "component (1)" and "component (2)," respectively. The hsp (or the immunostimulatory fragment thereof) and the HPV protein (or the antigenic fragment thereof) can be either simply combined in the same preparation or more closely associated by chemical conjugation or fusion (i.e., one can administer a fusion protein having the components described herein or a nucleic acid molecule that encodes it). When combined, conjugated, or fused, component (1) and component (2) would be administered simultaneously. Each component can, however, also be administered separately (e.g., sequentially), and component (2) can be administered without component (1). The method described above can include a step in which a subject who has, or who is suspected of having, a wart is identified (in the context of treating the subject, identification would be made before administration of the therapeutic agent begins). Physicians and others of ordinary skill in the art are well able to identify such subjects.

The methods of the invention can also be used to prevent a wart, in which case a subject who desires, or who would benefit from, wart prevention (rather than a subject who already has a wart) is identified.

The invention also features methods of treating a subject who has a disease or condition caused by an infection with an HPV of a first type (e.g., type 5, 6, 11, 18, 31, 33, 35, 45, 54, 60, or 70) by administering to the subject a composition containing (1) an hsp, or an immunostimulatory fragment thereof, and (2) a protein of an HPV of a second type (e.g., type 16) or an antigenic fragment thereof. That is, the HPV of the "first type" and the HPV of the "second type" are different from one another; they are of two different HPV types. The hsgp (or the immunostimulatory fragment thereof) and the HPV protein (or the antigenic fragment thereof) can be either simply combined in the same preparation or more intimately associated by chemical conjugation or fusion (i.e., one can administer a fusion protein having the components described herein or a nucleic acid molecule that encodes it). When combined, conjugated, or fused, component (1) and component (2) would be administered simultaneously. Each component can, however, also be administered separately (e.g., sequentially), and component (2) can be administered without component (1). Here again, the method can include a step in which a subject who has, or is suspected of having, an HPV infection (or a disease or condition associated therewith) is identified.

When a subject who is infected with a first HPV type is given a composition that includes an HPV of a second type, the method can be carried out before an HPV infection is typed, before it is manifest, or before it has occurred (i.e., one need not know the particular HPV type a subject has been infected with, or will be infected-with, before treatment or prophylaxis can begin). When the methods are preventative, they can include a step in which a subject who desires, or who would benefit from, prevention of an HPV infection is identified.

The compositions described herein can be administered in amounts that are sufficient to treat the wart (by, for example, reducing the size or altering the shape of the wart, or by ameliorating a symptom associated with a wart (e.g., the pain often associated with a plantar wart); when a subject has more than one wart, treatment can encompass reducing the number of warts). Similarly, the compositions described herein can be administered in amounts that are sufficient to treat the disease (e.g., cancer (such as cervical cancer or anal cancer) or other condition (e.g., dysplasia (such as cervical or anal dysplasia)) that is caused by, or associated with, an HPV infection.

Although warts are mentioned separately above, warts also constitute a condition caused by or associated with HPV. Physicians and others of ordinary skill in the art will recognize an effective "treatment" of a wart or an HPV-associated disease or condition when there is a diminution in an undesirable physiological affect associated with the wart or the disease or condition. The clinical and physiological manifestations of a wart, as well as those of a disease or condition associated with HPV infection, are discussed in, for example, Fauci et al., *Harrison's Principles of Internal Medicine*, 14th Edition, McGraw-Hill Press, New York, pp 302-303 and 1098-1100, 1998.

"Subjects" who can benefit from the methods described herein are those who can be infected by papilloma viruses (e.g., mammals such as humans, livestock (e.g., cows, horses, pigs, sheep, and goats), and domestic animals (e.g. cats and dogs)). The wart can be one that occurs on the subject's genitalia, skin, or internal organs (such as the warts that appear on the vocal cords in recurrent respiratory papillomatosis (RRP; also known as juvenile laryngeal papillomatosis (JLP) or adult-onset RRP)).

The invention further includes the use of one or more of the compositions described herein (including those that contain proteins, protein conjugates or fusion proteins, or the nucleic acid molecules that encode them) for the treatment of subject who has warts or a disease or conditions associated with (or caused by) an HPV infection, in accordance with the methods described herein. The invention further includes the use of one or more of such compositions in the manufacture of a medicament for the treatment of subject who has warts or a disease or conditions associated with (or caused by) an HPV infection, in accordance with the methods described herein.

An "antigenic fragment" of a protein (e.g. an HPV protein) is any portion of the protein that, when administered in accordance with the methods described herein, elicits, in a subject, an immune response that is either a fragment-specific or specific for the protein from which the fragment was obtained. The immune response can be either a humoral or a cell-mediated response. For example, an antigenic fragment can be an HLA class I peptide antigen, such as described below. One of ordinary skill in the art will recognize that the immune response desired in the context of the present invention can be generated not only by intact proteins and fragments thereof, but also by mutant proteins (e.g., those that contain one or more additions, substitutions (e.g. conservative amino acid substitutions) or deletions in their amino acid sequence). Mutant HPV antigens can be readily made and tested for their ability to work in the context of the present invention.

An "immunostimulatory fragment" of a protein (e.g., an hsp) is any portion of the protein that, when administered in accordance with the methods described herein, facilitates an immune response by an antigen. For example, if the immune response to an HPV protein is facilitated when that HPV protein is administered with (e.g., fused to) a fragment of an hsp, that fragment is an immunostimulatory fragment of an hsp. One of ordinary skill in the art will recognize that the immune response can also be facilitated by mutant hsps (e.g., hsps that contain one or more additions, substitutions (e.g., conservative amino acid substitutions) or deletions in the amino acid sequence). Mutant hsps can be readily made and tested for their ability to facilitate an immune response to an HPV antigen.

The methods of the invention provide an efficient means of: (1) treating or preventing warts and (2) treating or preventing a disease or condition caused by (or associated with) an infection with one HPV type with (i.e., using) a composition containing an HPV of another type. Consequently, a composition containing an HPV antigen of a single HPV type can be used in many, if not most, subjects, regardless of the HPV type with which they are infected (or with which they may become infected). It is surprising that HPV compositions are effective in these circumstances (i.e., circumstances requiring cross-reactivity). It has been thought that HPV antigens of one type cannot elicit an effective immune response against another type. Other features or advantages of the present invention will be apparent from the following detailed description, and also from the claims.

DETAILED DESCRIPTION

The invention relates to broadly effective HPV-based therapeutic agents containing an hsp and an HPV protein (e.g., a protein antigen). Without limiting the invention to methods in which HPV-based therapeutics exert their effect through a particular mechanism, the agents are thought to produce an immune response that improves warts and other conditions (e.g., dysplasia) and diseases (e.g., cancer) associated with HPV infections. Notably, while the compositions of the invention may contain an HPV protein from more than one HPV type, they can contain an HPV protein from only a single type. Moreover, compositions that contain an HPV protein from a single HPV type are useful in treating or preventing warts or other HPV-associated diseases or conditions that are caused by an HPV infection of another (i.e., a different) type. Various materials and procedures suitable for use in connection with the invention are discussed below.

Preparation of Fusion Proteins

The nucleic acid sequences encoding hsps and HPV proteins are known and available to those of ordinary skill in the art. Thus, nucleic acid constructs encoding fusion polypeptides useful in the methods of the invention can be readily prepared using routine methods (similarly, such nucleic acid molecules can be used to produce hsps and HPV proteins individually; the individual hsps and HPV proteins can then be physically combined (e.g. simply mixed together) or joined by chemical conjugation (see below) or via disulfide bonds). Examples of nucleic acid sequences that encode an hsp optionally fused to an antigen (e.g.; an HPV antigen) can be found in International Publication Nos. WO 89/12455, WO 94/29459, WO 98/23735, and WO 99/07860 and the references cited therein. Methods by which proteins, including fusion proteins, can be expressed and purified are discussed further below.

Preparation of Protein Conjugates

Component (1) and component (2) can also be joined by post-translational conjugation of individual hsps and individual HPV antigens. Methods for chemically conjugating two proteins (or portions thereof) are known in the art (see, e.g., the techniques described in Hermanson, *Bioconjugate Techniques*, Academic Press, San Diego, Calif., 1996; Lussow et al., *Eur. J. Immun.* 21:2297-2302, 1991; and Barrios et al., *Eur. J. Immun.* 22:1365-1372, 1992). Conjugates can be prepared by methods that employ cross-linking agents, such as glutaraldehyde (which becomes a part of the resultant conjugate), or that join component (1) and component (2) by disulfide bonds. One can use cysteine residues that are either naturally present or recombinantly inserted in the hsp, the HPV antigen, or both, to facilitate intermolecular disulfide bond formation. Compositions containing hsps or immunostimulatory fragments thereof(i.e. component (1)) that are non-covalently associated with HPV antigens can be produced as described in U.S. Pat. Nos. 6,048,530; 6,017,544;

6,017,540; 6,007,821; 5,985,270; 5,948,646; 5,935,576; 5,837,251; 5,830,464; or 5,750,119. See also, U.S. Pat. Nos. 5,997,873; 5,961,979; 6,030,618; 6,139,841; 6,156,302; 6,168,793; and International Publication No. WO 97/06821.

Regardless of the final configuration of the composition administered, component (1) and component (2) can include the following.

HPV Protein Antigens

Any HPV antigen is suitable for use in the compositions (e.g., the mixtures, conjugates and fusion proteins described herein) of the present invention. However, HPV antigens that express recognizable epitopes on the surface of an HPV infected cell should be especially useful. HPV expresses six or seven non-structural proteins and two structural proteins, and each of these can serve as a target in the immunoprophylactic or immunotherapeutic approaches described herein.

The viral capsid proteins L1 and L2 are the late structural proteins. L1 is the major capsid protein, the amino acid sequence of which is highly conserved among different HPV types. There are seven early non-structural proteins. Proteins E1, E2, and E4 play an important role in virus replication. Protein E4 also plays a role in virus maturation. The role of E5 is less well known. Proteins E6 and E7 are oncoproteins that are critical for viral replication, as well as for host cell immortalization and transformation.

Hsps

A variety of hsps have been isolated, cloned, and characterized from a diverse array of organisms (Mizzen, *Biotherapy* 10:173-189, 1998; as used herein, the term "heat shock protein(s)" or its abbreviation (hsp(s)) is synonymous with, or encompasses, the proteins referred to as "stress proteins"). Immunostimulatory hsps, or immunostimulatory fragments thereof, are suitable for use in the compositions described herein (e.g., as part of a fusion polypeptide). Hsp70, hsp60, hsp20-30, and hsp10 are among the major determinants recognized by host immune responses to infection by *Mycobacterium tuberculosis* and *Mycobacterium leprae*. In addition, hsp65 of Bacille Calmette Guerin (BCG), a strain of *Mycobacterium bovis*, was found to be an effective immunostimulatory agent, as described in the example below.

Families of hsp genes and hsps, any of which can be used as described herein for component (1), are well known in the art. These include, for example, Hsp100-200, Hsp100, Hsp90, Lon, Hsp70, Hsp60, TF55, Hsp40, FKBPs, cyclophilins, Hsp20-30, ClpP, GrpE, Hsp10, ubiquitin, calnexin, and protein disulfide isomerases. See, e.g., Macario, *Cold Spring Harbor Laboratory Res.* 25:59-70, 1995; Parsell et al., *Rev. Genet.* 27:437-496, 1993; and U.S. Pat. No. 5,232,833. The hsp can be, but is not limited to, a mammalian, bacterial, or mycobacterial hsp.

Grp170 (for glucose-regulated protein) is an example of an hsp in the hsp100-200 family. Grp170 resides in the lumen of the endoplasmic reticulum, in the pre-Golgi compartment, and may play a role in immunoglobulin folding and assembly.

Examples of hsps in the hsp100 family include mammalian Hsp110, yeast Hsp104, and the *E. coli* hsps ClpA, ClpB, ClpC, ClpX and ClpY.

Examples of hsps in the hsp90 family includes HtpG in *E. coli*, Hsp83 and Hsc83 in yeast, and Hsp90alpha, Hsp90beta, and Grp94 in humans. Hsp90 binds groups of proteins that are typically cellular regulatory molecules, such as steroid hormone receptors (e.g., glucocorticoid, estrogen, progesterone, and testosterone receptors), transcription factors, and protein kinases that play a role in signal transduction mechanisms. Hsp90 proteins also participate in the formation of large, abundant protein complexes that include other stress proteins.

Lon is a tetrameric ATP-dependent protease that degrades non-native proteins in *E. coli*.

Examples of hsps in the hsp70 family include Hsp72 and Hsc73 from mammalian cells, DnaK from bacteria or mycobacteria such as *Mycobacterium leprae*, *Mycobacterium tuberculosis*, and *Mycobacterium bovis* (such as Bacille-Calmette Guerin; referred to herein as hsp71), DnaK from *E. coli*, yeast, and other prokaryotes, and BiP and Grp78. Hsp70 is capable of specifically binding ATP as well as unfolded polypeptides and peptides; hsp70 participates in protein folding and unfolding as well as in the assembly and disassembly of protein complexes.

An example of an hsp from the Hsp60 family is Hsp65 from mycobacteria. Bacterial Hsp60 is also commonly known as GroEL. Hsp60 forms large homooligomeric complexes, and appears to play a key role in protein folding. Hsp60 homologues are present in eukaryotic mitochondria and chloroplasts.

Examples of hsps in the TF55 family include Tcpl, TRiC, and thermosome. These proteins typically occur in the cytoplasm of eukaryotes and some archaebacteria, and they form multi-membered rings, promoting protein folding. They are also weakly homologous to Hsp60.

Examples of hsps in the Hsp40 family include DnaJ from prokaryotes such as *E. coli* and mycobacteria and HSJ1, HDJ1, and Hsp40. Hsp40 plays a role as a molecular chaperone in protein folding, thermotolerance and DNA replication, among other cellular activities.

Examples of FKBPs include FKBP12, FKBP13, FKBP25, and FKBP59, Fprl and Nepl. These proteins typically have peptidyl-prolyl isomerase activity and interact with immunosuppressants such as FK506 and rapamycin. The proteins are typically found in the cytoplasm and the endoplasmic reticulum.

Examples of cyclophilins include cyclophilins A, B, and C. These proteins have peptidyl-prolyl isomerase activity and interact with the immunosuppressant cyclosporin A.

Hsp20-30 is also referred to as small Hsp. Hsp20-30 is typically found in large homooligomeric complexes or possibly heterooligomeric complexes. An organism or cell type can express several different types of small Hsps. Hsp20-30 interacts with cytoskeletal structures and may play a regulatory role in the polymerization/depolymerization of actin. Hsp20-30 is rapidly phosphorylated upon stress or exposure of resting cells to growth factors. Hsp20-30 homologues include alpha-crystallin.

ClpP is an *E. coli* protease involved in degradation of abnormal proteins. Homologues of ClpP are found in chloroplasts. ClpP forms a heterooligomeric complex with ClpA.

GrpE is an *E. coli* protein of about 20 kDa that is involved in the rescue of stress-damaged proteins as well as the degradation of damaged proteins. GrpE plays a role in the regulation of stress gene expression in *E. coli*.

Hsp10 examples include GroES and Cpn10. Hsp10 is found in *E. coli* and in the mitochondria and chloroplasts of eukaryotic cells. Hsp10 forms a seven-membered ring that associates with Hsp60 oligomers. Hsp10 is also involved in protein folding.

Ubiquitin has been found to bind proteins in coordination with the proteolytic removal of the proteins by ATP-dependent cytosolic proteases.

The stress proteins useful in the present invention can be obtained from enterobacteria (e.g., *E. coli*), mycobacteria (particularly *M. leprae*, *M. tuberculosis*, *M. vaccae*, *M. smegmatis*, and *M. bovis*), yeast, *Drosophila*, vertebrates (e.g., avians or mammals such as rodents or primates, including humans).

Protein Expression and Purification

Proteins can be recombinantly produced. More specifically, hsps (or fragments thereof) and HPV antigens (or fragments thereof), which can be administered separately, in combination, or after conjugation, as well as fusion proteins containing component (i) and component (2) can be recombinantly produced in bacteria, yeast, plants or plant cells, or animals or animal cells. For example, hsps, HPV antigens, and fusion proteins containing them can be produced by transformation (i.e., transfection, transduction, or infection) of a host cell with a nucleic acid sequence in a suitable expression vehicle. Suitable expression vehicles include plasmids, viral particles, and phage. For insect cells, baculovirus expression vectors are suitable. The entire expression vehicle, or a part thereof, can be integrated into the host cell genome. In some circumstances, it is desirable to employ an inducible expression vector, for example, the LACSWITCH® Inducible Expression System (Stratagene; La Jolla, Calif.).

Those skilled in the field of molecular biology will understand that any of a wide variety of expression systems can be used to provide recombinant proteins (e.g., fusion proteins) useful in the methods described herein. The precise host cell and vector used is not critical to the invention.

As noted above, component (1), component (2) and fusion proteins containing them can be produced by plant cells. For plant cells, viral expression vectors (e.g., cauliflower mosaic virus and tobacco mosaic virus) and plasmid expression vectors (e.g., Ti plasmid) are suitable. Such cells are available from a wide range of sources (e.g., the American Type Culture Collection, Manassas, Va.; see also, e.g., Ausubel et al., *Current Protocols in Molecular Biology*, John Wiley & Sons, New York, 1994). The methods of transformation and the choice of expression vehicle will depend on the host system selected. Transformation methods are described in, e.g., Ausubel (supra). Expression vehicles may be chosen from those provided in, e.g., Pouwels et al., *Cloning Vectors: A Laboratory Manual*, 1985, Supp. 1987.

The host cells harboring the expression vehicle can be cultured in conventional nutrient media adapted as needed for activation or repression of a chosen gene, selection of transformants, or amplification of a chosen gene.

Where appropriate or beneficial, the nucleic acid encoding a fusion protein can include a signal sequence for excretion of the fusion protein to, e.g., facilitate isolation of the protein from a cell culture. Specific initiation signals may also be required for efficient translation of inserted nucleic acid sequences. These signals include the ATG initiation codon and adjacent sequences. In some cases, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription or translation enhancer elements, (e.g., ones disclosed in Bittner et al., *Methods in Enzymol.* 153:516, 1987).

Component (1), component (2), and fusion proteins containing them can be soluble under normal physiological conditions. In addition, such fusion proteins can include one or more unrelated (i.e. a non-hsp, non-HPV) proteins (in whole or in part) to create an at least, tripartite fusion protein. The "third" protein can be one that facilitates purification, detection, or solubilization of the fusion protein, or that provides some other function. For example, the expression vector pUR278 (Ruther et al., *EMBO J.* 2:1791, 1983) can be used to create lacZ fusion proteins, and the pGEX vectors can be used to express foreign polypeptides as fusion proteins containing glutathione S-transferase (GST). In general, such fusion proteins are soluble and can be easily purified from lysed cells by adsorption-to glutathione-agarose beads, followed by elution in the presence of free glutathione. The pGEX vectors are designed to include thrombin or factor Xa protease cleavage sites so that the cloned target gene product can be released from the GST moiety. The "third" protein can also be an immunoglobulin Fc domain. Such a fusion protein can be readily purified using an affinity column. Of course, the fusion proteins used in the methods of the invention can include more than one component (1) and/or more than one component (2), and components (1) and (2) may be directly or indirectly linked (e.g., one or more amino acid residues may be present between them).

A protein (e.g. an hsp, an HPV antigen or an hsp-containing fusion protein) can be purified by utilizing an antibody to which the protein specifically binds. One of ordinary skill in the art can use affinity-based purification methods to purify proteins. For example, see Janknecht et al., *Proc. Natl. Acad. Sci. USA.* 88:8972, 1981, for purification of non-denatured fusion proteins expressed in human cell lines. In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns, and histidine-tagged proteins are selectively eluted with imidazole-containing buffers. The same procedure can be used for a bacterial culture.

Proteins, including fusion proteins (particularly those containing short antigenic fragments), can also be produced by chemical synthesis (e.g., by the methods described in *Solid Phase Peptide Synthesis*, 2nd ed., 1984 Tie Pierce Chemical Co., Rockford, Ill.).

Once isolated, the proteins can, if desired, be further purified and/or concentrated, so long as further processing does not impair their ability to elicit an immune response sufficient to be effective in the methods of the invention. A variety of methods for purifying and concentrating proteins are well known in the art (see, e.g., Fisher, *Laboratory Techniques In Biochemistry And Molecular Biology*, Work and Burdon, Eds., Elsevier, 1980), including ultracentrifugation and/or precipitation (e.g., with ammonium sulfate), microfiltration (e.g., via 0.45 μm cellulose acetate filters), ultrafiltration (e.g., with the use of a sizing membrane and recirculation filtration), gel filtration (e.g., columns filled with Sepharose CL-6B, CL-4B, CL-2B, 6B, 4B or 2B, Sephacryl S-400 or S-300, Superose 6 or Ultrogel A2, A4, or A6; all available from Pharmacia Corp.), fast protein liquid chromatography (FPLC), and high performance liquid chromatography (HPLC).

Cross-Reactive HPV Sequences

One of ordinary skill in the art can determine whether a composition containing an HPV antigen of a first type can be used to treat a subject who has been infected with a second type of HPV. The assays upon which such a determination can be based include predictive assays (e.g., those employing computer models) and biological assays (in which one actually tests for cross-reactivity). One or both types of assays can be used (not surprisingly, one would expect the results obtained in a predictive assay to be further tested in a biological assay). Examples of each follow.

One can test for cross-reactivity (i.e., the ability of a composition containing an HPV antigen of one type to effectively treat a subject who is infected with an HPV of another type, or who has a disease or condition associated with an HPV of another type) using well-established immunological methods. For example, bi-transgenic mice engineered to express the antigen binding region of the human MHC class I molecule and the human CD8 gene (Lustgarten et al., *Human Immunol.* 52:109, 1997; Vitiello et al., *J. Exp. Med.* 173:1007, 1991) can be used to demonstrate immune cross-reactivity.

More specifically, the HLA-A2/CD8 bi-transgenic mouse (Lustgarten et al., supra) can be used to demonstrate cross reactivity of cytotoxic T lymphocytes (CTL) raised to HPV16 E7 against peptides derived from the E7 protein of HPV6 and 11 using standard immunological techniques (see, e.g., Coligan et al. Eds., *Current Protocols in Immunology,* John Wiley & Sons, 1999). Briefly, mice are immunized one to three times at intervals of seven to 21 days with HspE7 fusion protein (based on the BCG Hsp65 and HPV16 E7 molecules). HspE7 is suspended in phosphate-buffered saline (PBS) and administered subcutaneously at a dose ranging from 1 µg to 1000 µg per mouse. Seven days following the final administration of HspE7, mice are sacrificed, their spleens removed, and the tissue dissociated into a single cell suspension. CTLs that are specific for HPV E7 are restimulated by the addition of HLA-A2 binding peptides derived from HPV16 E7, HPV6 E7 and HPV11 E7 to the culture medium at a concentration of 1 µM. The cells can be restimulated in, for example, 6-well plates, having a different peptide in each well. The peptides (e.g., the ten peptides) with the highest predicted HLA-A2 binding affinity, as defined by computer algorithm, can be used for each of HPV16, HPV6, and HPV11 (or any other HPV type; see Parker et al., *J. Immunol.* 152:163, 1994; the algorithm is also available on the internet through the BIMAS (Bioinformatics & Molecular Analysis Section) website of the National Institutes of Health (accessed on Jun. 26, 2001 at http://bimas.dcrt.nih.gov/). In addition, where different, the corresponding peptides from the other two HPV genotypes would also be used (i.e., HPV16 E7 peptide 11-20 and HPV6 and 11 peptides 11-20).

Following a period (e.g., one week) of restimulation in vitro, CTL activity would be measured by the lysis of T2 target cells pulsed with HLA-A2 binding peptides derived from HPV16 E7, HPV6 E7 and HPV11 E7. In addition, antigen-specific T lymphocytes, which recognize HLA-A2 binding peptides derived from HPV16 E7, HPV6 E7 and HPV11 E7, can be measured by ELISPOT analysis of IFN-γ secreting cells using previously described methods (Asal et al. *Clin. Diagn. Lab. Immunol.* 7:145, 2000). These analyses could be performed in mice transgenic for other HLA alleles.

Alternately, one can measure the ability of CTL, which are induced by immunization with HspE7, to cross-react with peptides derived from HPV6 or 11 E7 proteins in human HLA-A2 positive subjects undergoing therapy for genital warts using HspE7. Peripheral blood mononuclear cells (PBMC) can be-isolated from subjects (e.g., human patients) prior to treatment and several days (e.g., 7 days) following each treatment with HspE7. The cells can be analyzed by fluorogenic MHC-peptide complexes (tetramers, Altman et al., *Science* 274:94, 1996) or by ELISPOT analysis (Asal et al., *Clin. Diagn. Lab. Immunol.* 7:145, 2000). Cells can-be assayed directly from the peripheral blood and following in vitro restimulation as described by Youde et al. (*Cancer Res.* 60:365, 2000). For in vitro restimulation, $2 \times 10^6$/ml PBMC are cultured in RPMI1640 with 10% human AB serum (RAB) and peptide at a concentration of 10 µg/ml. Restimilating peptides would be derived from HPV16 E7 and would comprise the peptides (e.g., the ten peptides) with the highest predicted HLA-A2 binding affinity, as defined by computer algorithm (Parker et al., supra). On Day 4, 1 ml of RAB containing 25 units/ml of IL-2 is added to each well. On Day 6, 1 ml of medium is replaced with 1 ml of medium containing 10 units/ml of IL-2. On Day 7, irradiated autologous PBMC (fresh or frozen-then-thawed) are resuspended at $3 \times 10^6$ cells/ml in RAB containing 10 µg/ml peptide and 3 µg/ml $\beta_2$-microglobulin. Antigen presenting cells are allowed to adhere for two hours and are then washed to remove non-adherent cells before the addition of $1-2 \times 10^6$ effector cells/ml. On Day 9, one ml of RAB containing 25 units/ml of IL-2 is added to each well. On Day 13, the contents of the wells are divided into multiple plates and the medium (containing 10 units/ml of IL-2) is restored to the original volume. The cells are used on Day 14. For FACS analysis, tetramers are prepared as described previously (Altman et al., *Science* 274:94, 1996). The peptides used for loading the tetramers are HLA-A2 binding peptides derived from the E7 molecule of HPV16, HPV6 and HPV11. The peptides (e.g., the ten peptides) with the highest predicted HLA-A2 binding affinity, as defined by computer algorithm (Parker et al., supra) are used for each of HPV16, HPV6 and HPV11. In addition, where different, the corresponding peptides from the other two HPV genotypes are also used (i.e., HPV16 E7 peptide 11-20 and HPV 6 and 11 peptides 11-20). Fresh or restimulated PBMCs are stained with PE-labeled HPV-E7peptide tetramers and FITC labeled anti-CD8 antibody and analyzed by flow cytometry, as has been described. ELISPOT analysis of antigen-specific T lymphocytes that recognize HLA-A2 binding peptides derived from HPV16 E7, HPV6 E7 and HPV11 E7 present in fresh and restimulated PBMC is performed using previously described methods (Asal et al., *Clin. Diagn. Lab. Immunol.* 7:145, 2000). Likewise, these techniques can be applied to subjects with other HLA haplotypes.

In addition, it is possible to test the ability of human PBMC derived from HLA-A2 positive healthy volunteers not previously treated with HspE7, stimulated in vitro with HspE7 protein or peptides derived from HPV type 16 E7, to cross-react with cells pulsed with the corresponding peptides from the other two HPV genotypes (6 and 11). Cells are stimulated and assayed using procedures common to the art. Briefly, PBMC are isolated from peripheral blood, adherent cells are separated from non-adherent cells, and the adherent cells are cultured to generate dendritic cells (DC) as described in *Current Protocols in Immunology* (Coligan et al., Eds., John Wiley & Sons, pp 7.32.7-8, 1999). The non-adherent cells are cryopreserved in 90% FCS/10% DMSO for use at a later point in the assay.

For the stimulation, DC are pulsed with 50 µg/ml HspE7 or with 40 µg/ml of the appropriate peptide and 3 µg/ml $\beta_2$-microglobulin for 24 hours at 37° C., 5% $CO_2$ (Kawashima et al. *Human Immunol.* 59:1, 1998). The peptides used are HLA-A2 binding peptides derived from the E7 molecule of HPV16, HPV6 and HPV 11. The peptides (e.g., the ten peptides) with the highest predicted HLA-A2 binding affinity, as defined by computer algorithm (Parker et al., supra) are used for each of HPV16, HPV6 and HPV11. In addition, where different, the corresponding peptides from the other two HPV genotypes would also be used (ie HPV16 E7 peptide 11-20 and HPV 6 and 11 peptides 11-20). CD8$^+$ cells are isolated from cryopreserved, autologous non-adherent cells by positive selection using immunomagnetic beads (Miltenyi Biotec). Peptide/protein-loaded DC are irradiated at 4200 rads and mixed with autologous CD8$^+$ cells at a ratio of 1:20 in, e.g., 48-well plates containing $0.25 \times 10^5$ DC and $5 \times 10^5$ CD8$^+$ cells and 10 ng/ml of IL-7 in 0.5 mls of RAB. On days 7 and 14, the cells are restimulated with autologous peptide-pulsed adherent APC (Kawashirna et al., *Human Immunol.* 59:1, 1998). The cultures are fed every 2-3 days with 10 U/ml of hIL-2. HPV E7 peptide-specific T lymphocytes are analyzed by fluorogenic MHC-peptide complexes (tetramers, Altman et al., *Science* 274:94, 1996) or by ELISPOT analysis (Asal et al., *Clin. Diagn. Lab. Immunol.* 7:145, 2000) following 7 and 14 days of in vitro stimulation. For FACS analysis, tetramers are prepared as described previously (Altman et al. *Science* 274:-94, 1996). The peptides used for loading the tetramers would be HLA-A2 binding peptides derived from the E7 molecule of HPV16, HPV6 and HPV11, as described above. Peptide specific T lymphocytes are stained with PE-labeled HPV-E7 peptide tetramers and FITC labeled anti-CD8 antibody and analyzed by flow cytometry (Youde et al. *Cancer Res.* 60:365, 2000). ELISPOT analysis of antigen-specific T lymphocytes, which recognize HLA-A2 binding peptides derived from HPV16 E7, HPV6 E7 and HPV11 E7, is performed using previously described methods (Asal et al. *Clin. Diagn. Lab. Immunol.* 7:145, 2000). Likewise, these techniques could be applied to subjects with other HLA haplotypes.

Administration of Compositions

The invention includes compositions containing at least one HPV protein antigen (e.g. an HPV protein antigen (or an antigenic fragment thereof), an HPV protein antigen mixed with or conjugated to an hsp (or an immunostimulatory fragment thereof) or a fusion protein containing an HPV protein antigen (or an antigenic fragment thereof) and an hsp (or an immunostimulatory fragment thereof). Optionally, these proteins can be suspended in a pharmaceutically acceptable carrier, such as a diluent (e.g., PBS) or a bicarbonate solution (e.g., 0.24 M $NaHCO_3$). Useful carriers are selected on the basis of the mode and route of administration and on standard pharmaceutical practice. Suitable pharmaceutical carriers and diluents, as well as pharmaceutical necessities for their use, are described in Remington's Pharmaceutical Sciences. An adjuvant, for example, a cholera toxin, *Escherichia coli* heat-labile enterotoxin (LT), a liposome, or an immunestimulating complex (ISCOM), can also be included.

The protein(s) (e.g., the fusion protein) need not be administered to the subject directly. Instead, a nucleic acid sequence encoding the protein can be administered; the protein being expressed in the subject in vivo. The nucleic acid can be a part of a vector (such as a viral vector, for example, a part of a viral vector genome), or encapsulated, for example, in liposomes. Alternatively, the nucleic acid can be delivered as a naked nucleic acid.

The compositions can be formulated as a solution, suspension, suppository, tablet, granules, a powder, a capsule, ointment, or cream. As noted above, in preparing these compositions, one or more pharmaceutical carriers can be included. Additional examples of pharmaceutically acceptable carriers or other additives include solvents (e.g., water or physiological saline), solubilizing agents (e.g., ethanol, polysorbates, or Cremophor EL®), agents for rendering isotonicity, preservatives, antioxidizing agents, excipients (e.g., lactose, starch, crystalline cellulose, mannitol, maltose, calcium hydrogen phosphate, light silicic acid anhydride, or calcium carbonate), binders (e.g., starch, polyvinylpyrrolidone,.hydroxypropyl cellulose, ethyl cellulose, carboxy methyl cellulose, or gum arabic), lubricants (e.g., magnesium stearate, talc, or hardened oils), or stabilizers (e.g., lactose, mannitol, maltose, polysorbates, macrogels, or polyoxyethylene-hardened castor oils). If necessary (or desired), glycerin, dimethylacetamide, sodium lactate, a surfactant, sodium hydroxide, ethylenediamine, ethanolamine, sodium bicarbonate, arginine, meglumine, or trisaminomethane can be added. Biodegradable polymers such as poly-D,L-lactide-co-glycolide or polyglycolide can be used as a bulk matrix if slow release of the composition is desired (see, for example, U.S. Pat. Nos. 5,417,986, 4,675,381, and 4,450,150). Pharmaceutical preparations such as solutions, tablets, granules or capsules can be formed with these components. If the composition is administered orally, flavorings and colors can be added.

The therapeutic compositions can be administered via any appropriate route, for example, intravenously, intraarterially, topically, intraperitoneally, intrapleurally, orally, subcutaneously, intramuscularly, intradermally, sublingually, intraepidermally, nasally, intrapulmonarily (e.g., by inhalation), vaginally, or rectally.

The amount of the composition administered will depend, for example, on the particular composition, whether an adjuvant is co-administered with the composition, the type of adjuvant co-administered, the mode and frequency of administration, and the desired effect (e.g., protection or treatment). Dosages are routinely determined by those of ordinary skill in the art in the course of developing drugs or prophylactic agents. In general, the compositions of the present invention are administered in amounts ranging between 1 µg and 100 mg per adult human dose. If adjuvants are administered with the compositions, amounts ranging between 1 ng and 1 mg per adult human dose can generally be used. Administration is repeated as necessary, as can be determined by one of ordinary skill in the art. For example, a priming dose can be followed by three booster doses at weekly or monthly intervals. A booster shot can be given at 3 to 12 weeks after the first administration, and a second booster can be given 3 to 12 weeks later, using the same formulation. Serum or T cells can be taken from the subject for testing the immune response elicited by the composition against the HPV antigen included in, for example, the fusion protein or protein conjugate. Methods of assaying antibodies or cytotoxic T cells against a specific antigen are well known in the art. Additional boosters can be given as needed. By varying the amount of, for example, fusion protein in the composition, the immunization protocol can be optimized for eliciting a maximal immune response.

Of course, the proteins described herein can also be delivered by administering a nucleic acid, such as a viral vector (e.g., a retroviral or adenoviral vector).

Without further elaboration, it is believed that one skilled in the art can, based on the above disclosure and the example below, utilize the present invention to its fullest extent. The following example is to be construed as merely illustrative of how one skilled in the art can isolate and use fusion polypeptides, and is not limitative of the remainder of the disclosure in any way. All publications, including U.S. patents and published International applications, cited herein are hereby incorporated by reference

EXAMPLE

A fusion polypeptide containing the *M. bovis* BCG Hsp65 coupled to the E7 protein of HPV type 16 was recombinantly produced and formulated as described in WO 99/07860. Hsp65 is a member of the Hsp60 family of stress proteins. In the course of a human clinical trial for testing the efficacy of this fusion polypeptide in the treatment of anal high-grade squamous intraepithelial lesions (HSIL), the following observation was made.

Twenty-two patients participated in a randomized, double-blind, placebo-controlled, multicenter trial of HspE7 in the treatment of anal HSIL. Eligible patients had biopsy-confirmed anal HSIL and were negative for human immunodeficiency virus (HIV). Patients were typed for HPV using cells obtained from an anal swab, but were not required to have HPV-16. Individual lesions were not typed for HPV. Patients received three subcutaneous injections of either 100 µg of HpsE7 or placebo at monthly intervals. They were assessed for treatment response by anal Pap smears, high-resolution anoscopy (HRA) with biopsy, and global physician assessment. Non-responders (i.e., those with persistent anal HSIL) after 12 or 24 weeks in the controlled trial were allowed to crossover to an open-label trial where they received three injections of 500 µg of HspE7 at monthly intervals. The treatment assignment was double-blinded in the placebo-controlled trial, and the blind has not been broken.

To determine the HPV type(s) infecting patients, a Dacron swab was used to collect specimens from the anus of patients at the screening visit of the randomized, placebo-controlled trial, just before biopsy. After transport in Sample Transport Medium (Digene), DNA was isolated and used to determine HPV type. Briefly, the consensus primer set MY09/MY11 was used to amplify HPV DNA by polymerase chain reaction (PCR). Following the amplification step, samples were blotted onto nylon membrane and probed with biotin-labeled oligonucleotides specific for 29 different HPV types (6, 11, 16, 18, 26, 31, 32, 33, 35, 39, 40, 45, 51, 52, 53, 54, 55, 56, 58, 59, 61, 66, 68, 69, 70, 73, AE2, Pap155, and Pap291), plus a pooled probe containing primers for 10 HPV types (2, 13, 34, 42, 57, 62, 64, 67, 72, and W13B). Samples-that produced a "dot blot" were scored positive or negative for HPV type by comparison to standardized controls using a 5-point scale; a score of 1 or greater was positive.

To verify that the PCR was successful, a beta-globin control amplification and probe detection was performed for each sample. If the sample was not positive for the presence of beta-globin, the PCR step was considered a technical failure. If the consensus probe did not result in a score of 2 or more, the sample was considered "HPV negative."

At the time of their entry into the open label trial, 14 of the 22 patients (64%) had anogenital warts that had persisted throughout the prior double-blind trial in which they received three monthly injections of either 100 µg of HspE7 or placebo. Of these 14 patients, 8 patients (57%) had worsened, 4 patients (29%) had no change, and 2 patients (14%) improved (one dramatically and the other minimally) by the time they crossed over to the open label trial. An additional patient had condyloma present at the start of the double-blind trial that resolved before the start of the open-label trial, and is omitted from this analysis, as are the seven other patients who had no detectable warts during either trial. Condylomata were present within the anorectal canal in all 14 patients (100%) and on the perianal skin as well in 6 of 14 patients (43%). Of the 14 patients with warts at the beginning of the open label trial, the site investigator determined that surgical ablation was needed for 11 (79%) patients, local ablation (e.g.,-liquid-nitrogen,r:-etrocautery) was needed for 2 patients (14%), and topical treatment (i.e., imiquimod) was needed for 1 patient (7%). These patients elected to postpone the site investigator's recommended treatment, consenting instead to receive three injections of HspE7 500 µg at monthly intervals in the open label trial.

One month after the final treatment with 500 µg of HspE7, 2 patients (14%) had no detectable warts, 11 patients (79%) had a reduction in the size or number of warts as compared with their status upon entry into the open-label trial, and 1 patient (7%) experienced an increase in wart size (Table 1). By the time of the primary evaluation point of the open label trial (4 months after the final dose) one additional patient experienced an improvement from partial to complete response (i.e., no visible warts), giving a total of three (21%) complete responders (Table 1). None of these responders relapsed during the six months of evaluation in the open label trial. Ten patients (71%) continued to exhibit improvement in partial response (i.e., warts reduced further in size significantly with continued diminution of the extent of treatment needed to remove the remaining warts). The one non-responder (7%) did not improve by the end of the open-label trial.

TABLE 1

Response Summary for Anogenital Warts After Treatment with HspE7

| Outcome | Number (%) of Patients | |
|---|---|---|
| | Week 12* (n = 14) | Week 24† (n = 14) |
| Complete responder | 2 (14) | 3 (21) |
| Partial responder | 11 (79) | 10 (71) |
| Non-responder | 1 (7) | 1 (7) |

*One month after the final treatment with 500 µg of HspE7.
†Four months after the final treatment with 500 µg of HspE7.

At the end of the trial, the site investigator did not recommend further treatment for the three complete responders. As listed in Table 2, the site investigator's recommended treatment for the partial responders was ablative therapy (6 of 14, 43%) or treatment with a topical agent (4 of 14, 29%); additional surge:y.was recommended for the non-responder (1 of 14, 7%). All 22 patients entered a registry protocol for long-term follow-up of their response and they consented to postpone the investigator's recommended treatment.

TABLE 2

Anogenital Wart Response Assessments and Clinician-Recommended Treatment

| Patient Number | Baseline* | | Week 12† | | Week 24‡ |
|---|---|---|---|---|---|
| | Recommended Treatment | Wart Response | Recommended Treatment | Wart Response | Recommended Treatment |
| 003 | Surgery | CR | Topical | CR | None |
| 004 | Surgery | PR | Ablation | PR | Ablation |
| 005 | Topical | PR | Topical | CR | None |
| 006 | Surgery | PR | Surgery | PR | Ablation |
| 008 | Ablation | PR | Topical | PR | Topical |
| 009 | Surgery | PR | Ablation | PR | Topical |
| 010 | Surgery | PR | Ablation | PR | Ablation |
| 011 | Surgery | CR | Topical | CR | None |
| 014 | Surgery | PR | Topical | PR | Topical |
| 016 | Surgery | Worse | Surgery | Worse | Surgery |
| 017 | Ablation | PR | Topical | PR | Topical |
| 020 | Surgery | PR | Ablation | PR | Ablation |
| 021 | Surgery | PR | Ablation | PR | Ablation |
| 022 | Surgery | PR | Ablation | PR | Ablation |

*Baseline refers to the beginning of the open-label trial.
†One month after the final treatment with 500 µg of HspE7.
‡Four months after the final treatment with 500 µg of HspE7.
Abbreviations: CR = complete response; PR = partial response In all 14 patients diagnosed with anogenital warts, HPV DNA of multiple HPV types was detected in anal swab specimens during screening for the first, randomized, controlled trial (Table 3). HPV-6 and/or 11 were present in 12 patients (86%). One patient had only HPV-16 and related types and another patient could not be typed. Three of the 14 patients (21%) were positive for HPV-16. Most patients whose warts improved (11 of 13, 85%) did not have HPV-16. The non-responder also did not have HPV-16 (see Table 3).

TABLE 3

HPV Types in Patients with Anogenital Warts

| Patient Number | HPV Type in Anal Swab Specimens, at Screen* | Wart Response at Week 24† |
|---|---|---|
| 003 | 6, 11, 16 | CR |
| 004 | 6, 54 | PR |
| 005 | 6, 70 | CR |
| 006 | 6, 11, 45 | PR |
| 008 | 16, 31, 55 | PR |
| 009 | 6, 11, 59 | PR |
| 010 | 6, 11, 45, 54 | PR |
| 011 | HPV positive, type unknown | CR |
| 014 | 6, 11 | PR |
| 016 | 11, 61 | Worse |
| 017 | HPV negative | PR |
| 020 | 6, 11, 16 | PR |
| 021 | 6, 31, 53, 58, 59, 61, 66 | PR |
| 022 | 6 | PR |

*Screening visit of the randomized, placebo-controlled clinical trial.
†Four months after the final treatment with 500 µg of HspE7.
Abbreviations: HPV = human papillomavirus; CR = complete response; PR = partial response In this open-label, crossover trial of HspE7 (500 µg at 3 monthly intervals) involving patients with persistent anal HSIL and concomitant anogenital warts, 3 of the 14 patients (17%) who had warts at baseline no longer had warts 4 months after the final dose. Another 10 patients (71%) experienced improvement in their symptoms (i.e., warts reduced in size significantly and continued diminution of the extent of treatment needed to remove the remaining warts). One patient (7%) did not improve over the course of the trial and additional surgery was recommended by the site investigator.

Before enrollment in the open-label trial, most patients at this trial site would have undergone surgical intervention for the removal of their warts (11 of 14, 79%). By the end of the trial, surgical treatment was recommended for only one patient. Local ablative therapy (e.g., liquid nitrogen, electrocautery) was recommended for six patients (43%) and treatment with a topical agent (e.g., imiquimod) was recommended for four patients (29%). Three patients did not need further treatment.

Responses appear to be progressive over 6 months and no responder relapsed over this period. Gradual and progressive resolution of condyloma is in-keeping with what one would expect from an immunologic host response after induction of cell-mediated immunity by HspE7.

Two patients in the double-blind trial had some improvement in their condyloma before entering the open-label trial. To date, we have not broken the blind and do not know whether these patients received 100 µg of HspE7 or placebo. However, based on the response observed in the open-label trial of three monthly injections of 500 µg of HspE7, it appears that the higher dose is more active than 100 µg.

HPV-16 DNA was detected in anal swab specimens from only 3. of the 13 patients (23%) whose warts improved after treatment with HspE7. DNA from HPV-6, HPV-11, or both, was detected in most of the patients whose warts responded to treatment with HspE7. These data suggest that there is immunologic cross-reactivity between these HPV types in their response to HspE7.

In summary, the results presented here suggest that HspE7 is broadly active in anogenital warts. This activity does not appear to be limited to HPV-16 positive patients, but crosses multiple HPV types. It is predicted that HspE7 will be active in the treatment of HPV-induced diseases of the anogenital region and that this activity will not be limited to HPV-16 positive patients.

The observations reported here suggest that therapeutic treatment with HspE7 may constitute a new, simple, and non-surgical treatment for anogenital warts that, at a minimum, would lessen wart burden, thereby reducing the extent of treatment and resultant morbidity. Internal anorectal disease often requires additional treatment that can be quite painful and debilitating. Any treatment that provides a even partial response that reduces or eliminates the amount or extent of "surgical" or ablative therapy translates into a reduction in morbidity, less loss of time from work, and improved quality of life.

These results indicate that a heat shock protein/HPV type 16 antigen composition is effective in eliminating or reducing warts, which are thought to be caused predominantly by HPV types 6 and 11. Of significant import are the observations that (1) warts can be treated at all with an HPV-based composition, and (2) a HPV type 16 composition was effective in treating a condition presumably caused by a HPV other than type 16. The latter cross-reactive result was wholly unexpected, given the generally held belief that a type-specific composition could only-elicit a type-specific immune response.

To elucidate a possible mechanism for the observed cross-reactivity of the fusion polypeptide, theoretic binding was calculated for various HLA class I molecules and E7 peptides of HPV types 16, 6, and 11. The $T_{1/2}$ of dissociation was calculated using the algorithm described in Parker et al., *J. Immunol.* 152:163, 1994 (see also the website described above). The data is summarized in Table 4.

TABLE 4

| HLA Type | HPV Type 16 | | | HPV Type 6 | | | HPV Type 11 | | |
|---|---|---|---|---|---|---|---|---|---|
| | start | sequence | $T_{1/2}$ | start | sequence | $T_{1/2}$ | start | sequence | $T_{1/2}$ |
| A1 | 44 | QAEPDRAHY (SEQ ID NO:1) | 900 | 44 | DSQPLKQHY (SEQ ID NO:51) | 8 | 44 | DAQPLTQHY (SEQ ID NO:106) | 5 |
| | 16 | QPETTDLYCY (SEQ ID NO:2) | 23 | 17 | PPDPVGLHCY (SEQ ID NO:52) | 6 | 17 | PPDPVGLHCY (SEQ ID NO:52) | 6 |
| | | | | | | | 68 | VVECTDGDIR (SEQ ID NO:107) | 9 |
| A_0201 | 11 | YMLDLQPET (SEQ ID NO:3) | 375 | | | | | | |

TABLE 4-continued

| HLA Type | \multicolumn{3}{c}{HPV Type 16} | \multicolumn{3}{c}{HPV Type 6} | \multicolumn{3}{c}{HPV Type 11} |
|---|---|---|---|---|---|---|---|---|---|
| | start | sequence | $T_{1/2}$ | start | sequence | $T_{1/2}$ | start | sequence | $T_{1/2}$ |
| | 7 | TLHEYMLDL (SEQ ID NO:4) | 201 | 7 | TLKDIVLDL (SEQ ID NO:53) | 7 | 7 | TLKDIVLDL (SEQ ID NO:53) | 7 |
| | 82 | LLMGTLGIV (SEQ ID NO:5) | 54 | 82 | LLLGTLNIV (SEQ ID NO:54) | 412 | 82 | LLLGTLNIV (SEQ ID NO:54) | 412 |
| | | | | 28 | QLVDSSEDEV (SEQ ID NO:55) | 140 | 28 | QLEDSSEDEV (SEQ ID NO:108) | 9 |
| | 78 | TLEDLLMGT (SEQ ID NO:4) | 5 | 79 | VQQLLLGTL (SEQ ID NO:56) | 1 | 78 | QLQDLLLGT (SEQ ID NO:109) | 70 |
| A_0205 | 7 | TLHEYMLDL (SEQ ID NO:4) | 50 | 7 | TLKDIVLDL (SEQ ID NO:53) | 4 | 7 | TLKDIVLDL (SEQ ID NO:53) | 4 |
| | 11 | YMLDLQPET (SEQ ID NO:3) | 27 | 12 | VLDLQPPDPV (SEQ ID NO:57) | 1 | 12 | VLDLQPPDPV (SEQ ID NO:57) | 1 |
| | 82 | LLMGTLGIV (SEQ ID NO:5) | 20 | 82 | LLLGTLNIV (SEQ ID NO:54) | 20 | 82 | LLLGTLNIV (SEQ ID NO:54) | 20 |
| | 78 | TLEDLLMGT (SEQ ID NO:6) | 2 | 79 | VQQLLLGTL (SEQ ID NO:56) | 19 | 78 | QLQDLLLGT (SEQ ID NO:109) | 42 |
| | 5 | TPTLHEYML (SEQ ID NO:7) | 0 | 5 | HVTLKDIVL (SEQ ID NO:58) | 14 | 5 | LVTLKDIVL (SEQ ID NO:110) | 24 |
| A24 | 56 | TFCCKCDSTL (SEQ ID NO:8) | 20 | | | | | | |
| | 51 | HYNIVTFCC (SEQ ID NO:9) | 11 | 51 | HYQIVTCCC (SEQ ID NO:59) | 11 | 51 | HYQILTCCC (SEQ ID NO:111) | 9 |
| | 24 | CYEQLNDSS (SEQ ID NO:10) | 9 | 25 | CYEQLVDSS (SEQ ID NO:60) | 9 | 25 | CYEQLEDSS (SEQ ID NO:112) | 9 |
| | 4 | DTPTLHEYML (SEQ ID NO:11) | 6 | 5 | HVTLKDIVL (SEQ ID NO:58) | 4 | 4 | RLVTLKDIVL (SEQ ID NO:113) | 12 |
| | | | | 39 | EVDGQDSQPL (SEQ ID NO:61) | 5 | 39 | KVDKQDAQPL (SEQ ID NO:114) | 10 |
| A3 | 88 | GIVCPICSQK (SEQ ID NO:12) | 14 | 88 | NIVCPICAPK (SEQ ID NO:62) | 5 | 88 | NIVCPICAPK (SEQ ID NO:62) | 5 |
| | 7 | TLHEYMLDL (SEQ ID NO:4) | 8 | 7 | TLKDIVLDL (SEQ ID NO:53) | 5 | 7 | TLKDIVLDL (SEQ ID NO:53) | 5 |
| A68.1 | 68 | CVQSTHVDIR (SEQ ID NO:13) | 200 | 68 | VVQCTETDIR (SEQ ID NO:63) | 200 | 68 | VVECTDGDIR (SEQ ID NO:107) | 200 |
| | 89 | IVCPICSQK (SEQ ID NO:14) | 180 | 89 | IVCPICAPK (SEQ ID NO:64) | 180 | 89 | IVCPICAPK (SEQ ID NO:64) | 180 |
| A_1101 | 89 | IVCPICSQK (SEQ ID NO:14) | 2.0 | 89 | IVCPICAPK (SEQ ID NO:64) | 2 | 89 | IVCPICAPK (SEQ ID NO:64) | 2.0 |
| | 68 | CVQSTHVDIR (SEQ ID NO:13) | 1.8 | 68 | VVQCTETDIR (SEQ ID NO:63) | 1 | 68 | VVECTDGDIR (SEQ ID NO:63) | 0.6 |
| A_3101 | 69 | VQSTHVDIR (SEQ ID NO:15) | 4.0 | 69 | VQCTETDIR (SEQ ID NO:65) | 2 | 68 | VVECTDGDIR (SEQ ID NO:107) | 2.0 |
| | 88 | GIVCPICSQK (SEQ ID NO:12) | 0.4 | 88 | NIVCPICAPK (SEQ ID NO:62) | 0 | 88 | NIVCPICAPK (SEQ ID NO:62) | 0.4 |

TABLE 4-continued

| HLA Type | HPV Type 16 | | | HPV Type 6 | | | HPV Type 11 | | |
|---|---|---|---|---|---|---|---|---|---|
| | start | sequence | $T_{1/2}$ | start | sequence | $T_{1/2}$ | start | sequence | $T_{1/2}$ |
| A_3302 | 68 | CVQSTHVDIR (SEQ ID NO:13) | 15 | 68 | VVQCTETDIR (SEQ ID NO:107) | 15 | 68 | VVECTDGDIR (SEQ ID NO:107) | 15 |
| | 58 | CCKCDSTLR (SEQ ID NO:16) | 3 | 58 | CCGCDSNVR (SEQ ID NO:66) | 3 | 58 | CCGCDSNVR (SEQ ID NO:66) | 3 |
| B14 | 65 | LRLCVQSTHV (SEQ ID NO:17) | 30 | 65 | VRLVVQCTE (SEQ ID NO:67) | 1 | 65 | VRLVVECTD (SEQ ID NO:115) | 1 |
| | 4 | DTPTLHEYML (SEQ ID NO:11) | 18 | 3 | GRHVTLKDI (SEQ ID NO:68) | 12 | 3 | GRLVTLKDI (SEQ ID NO:116) | 60 |
| | 5 | TPTLHEYML (SEQ ID NO:7) | 3 | 6 | VTLKDIVLDL (SEQ ID NO:69) | 10 | 6 | VTLKDIVLDL (SEQ ID NO:69) | 15 |
| | 76 | RTLEDLLMGT (SEQ ID NO:18) | 1 | 76 | IREVQQLLL (SEQ ID NO:70) | 4 | 76 | IRQLQDLLL (SEQ ID NO:117) | 20 |
| B40 | 36 | DEIDGPAGQA (SEQ ID NO:19) | 120 | 35 | DEVDEVDGQ (SEQ ID NO:71) | 2 | 35 | DEVDKVDKQ (SEQ ID NO:118) | 2 |
| | 74 | VDIRTLEDL (SEQ ID NO:20) | 10 | 74 | TDIREVQQL (SEQ ID NO:72) | 10 | 74 | GDIRQLQDL (SEQ ID NO:119) | 20 |
| | 77 | RTLEDLLMGT (SEQ ID NO:18) | 0 | 77 | REVQQLLLGT (SEQ ID NO:73) | 16 | | | |
| | 87 | LGIVCPICS (SEQ ID NO:21) | 0 | 87 | LNIVCPICA (SEQ ID NO:74) | 2 | 87 | LNIVCPICA (SEQ ID NO:74) | 2 |
| B60 | 79 | LEDLLMGTL (SEQ ID NO:22) | 176 | 79 | VQQLLLGTL (SEQ ID NO:56) | 2 | 79 | LQDLLLGTL (SEQ ID NO:120) | 2 |
| | 20 | TDLYCYEQL (SEQ ID NO:23) | 44 | 21 | VGLHCYEQL (SEQ ID NO:75) | 9 | 21 | VGLHCYEQL (SEQ ID NO:75) | 9 |
| | 74 | VDIRTLEDL (SEQ ID NO:20) | 40 | 74 | TDIREVQQL (SEQ ID NO:72) | 44 | 74 | GDIRQVQDL (SEQ ID NO:121) | 44 |
| | | | | 40 | VDGQDSQPL (SEQ ID NO:76) | 20 | 40 | VDKQDAQPL (SEQ ID NO:122) | 20 |
| B61 | 36 | DEIDGPAGQA (SEQ ID NO:19) | 40 | 35 | DEVDEVDG (SEQ ID NO:77) | 1 | 35 | DEVDKVDKQ (SEQ ID NO:118) | 1 |
| | 34 | EEDEIDGPA (SEQ ID NO:24) | 20 | 33 | SEDEVDEV (SEQ ID NO:78) | 40 | 33 | SEDEVDKV (SEQ ID NO:123) | 40 |
| | | | | 72 | TETDIREV (SEQ ID NO:79) | 80 | 72 | TDGDIRQL (SEQ ID NO:24) | 1 |
| | 29 | NDSSEEEDEI (SEQ ID NO:25) | 1 | | | | 29 | LEDSSEDEV (SEQ ID NO:125) | 40 |
| B62 | 15 | LQPETTDLY (SEQ ID NO:26) | 88 | 15 | LQPPDPVGL (SEQ ID NO:80) | 6 | 15 | LQPPDPVGL (SEQ ID NO:80) | 6 |
| | 43 | GQAEPDRAHY (SEQ ID NO:27) | 44 | 44 | DSQPLKQHY (SEQ ID NO:51) | 1 | 44 | DAQPLTQHY (SEQ ID NO:106) | 5 |
| | 7 | TLHEYMLDL (SEQ ID NO:4) | 3 | 7 | TLKDIVLDL (SEQ ID NO:53) | 16 | 7 | TLKDIVLDL (SEQ ID NO:53) | 16 |
| | 82 | LLMGTLGIV (SEQ ID NO:5) | 2 | 83 | LLGTLNIVC (SEQ ID NO:81) | 11 | 83 | LLGTLNIVC (SEQ ID NO:81) | 11 |

TABLE 4-continued

| HLA Type | HPV Type 16 start | sequence | T₁/₂ | HPV Type 6 start | sequence | T₁/₂ | HPV Type 11 start | sequence | T₁/₂ |
|---|---|---|---|---|---|---|---|---|---|
| B7 | 5 | TPTLHEYML (SEQ ID NO:7) | 80 | 5 | HVTLKDIVL (SEQ ID NO:58) | 20 | 5 | LVTLKDIVL (SEQ ID NO:110) | 20 |
|  | 75 | DIRTLEDLL (SEQ ID NO:28) | 40 | 75 | DIREVQQLL (SEQ ID NO:82) | 40 | 75 | DIRQLQDLL (SEQ ID NO:126) | 40 |
|  | 46 | EPDRAHYNI (SEQ ID NO:29) | 2 | 46 | QPLKQHYQI (SEQ ID NO:83) | 8 | 46 | QPLTQHYQIL (SEQ ID NO:127) | 80 |
| B8 | 58 | CCKCDSTLRL (SEQ ID NO:30) | 16 | 58 | CCGCDSNVRL (SEQ ID NO:84) | 1 | 58 | CCGCDSNVRL (SEQ ID NO:84) | 1 |
|  | 75 | DIRTLEDL (SEQ ID NO:31) | 8 | 75 | DIREVQQL (SEQ ID NO:85) | 12 | 75 | DIRQLQDLL (SEQ ID NO:126) | 8 |
|  |  |  |  | 7 | TLKDIVLDL (SEQ ID NO:53) | 12 | 7 | TLKDIVLDL (SEQ ID NO:53) | 12 |
| B_2702 | 48 | DRAHYNIVTF (SEQ ID NO:32) | 60 | 49 | KQHYQIVTC (SEQ ID NO:86) | 6 | 49 | TQHYQILTC (SEQ ID NO:128) | 2 |
|  | 76 | IRTLEDLLM (SEQ ID NO:33) | 20 | 76 | IREVQQLLL (SEQ ID NO:70) | 60 | 76 | IRQLQDLLL (SEQ ID NO:117) | 60 |
|  | 65 | LRLCVQSTH (SEQ ID NO:34) | 20 | 65 | VRLVVQCTET (SEQ ID NO:87) | 20 | 65 | VRLVVECTD (SEQ ID NO:115) | 2 |
|  | 2 | HGDTPTLHEY (SEQ ID NO:35) | 1 | 3 | GRHVTLKDIV (SEQ ID NO:88) | 20 | 3 | GRLVTLKDIV (SEQ ID NO:129) | 20 |
| B_2705 | 76 | IRTLEDLLM (SEQ ID NO:33) | 600 | 76 | IREVQQLLL (SEQ ID NO:70) | 2000 | 76 | IRQLQDLLL (SEQ ID NO:117) | 2000 |
|  | 65 | LRLCVQSTHV (SEQ ID NO:17) | 600 | 65 | VRLVVQCTET (SEQ ID NO:87) | 200 | 65 | VRLVVECTD (SEQ ID NO:115) | 20 |
|  |  |  |  | 3 | GRHVTLKDIV (SEQ ID NO:88) | 600 | 3 | GRLVTLKDIV (SEQ ID NO:129) | 600 |
| B_3501 | 5 | TPTLHEYML (SEQ ID NO:7) | 20 | 5 | HVTLKDIVL (SEQ ID NO:58) | 1 | 5 | LVTLKDIVL (SEQ ID NO:110) | 1 |
|  | 16 | QPETTDLYCY (SEQ ID NO:2) | 18 | 15 | LQPPDPVGL (SEQ ID NO:80) | 2 | 15 | LQPPDPVGL (SEQ ID NO:80) | 2 |
|  | 43 | GQAEPDRAHY (SEQ ID NO:27) | 6 | 44 | DSQPLKQHY (SEQ ID NO:51) | 10 | 44 | DAQPLTQHY (SEQ ID NO:106) | 6 |
|  | 46 | EPDRAHYNIV (SEQ ID NO:36) | 1 | 46 | QPLKQHYQI (SEQ ID NO:83) | 8 | 48 | QPLTQHYQIL (SEQ ID NO:127) | 20 |
| B_3701 | 74 | VDIRTLEDLL (SEQ ID NO:37) | 200 | 74 | TDIREVQQLL (SEQ ID NO:89) | 300 | 74 | GDIRQLQDLL (SEQ ID NO:130) | 200 |
|  | 20 | TDLYCYEQL (SEQ ID NO:23) | 40 | 21 | VGLHCYEQLV (SEQ ID NO:90) | 1 | 21 | VGLHCYEQL (SEQ ID NO:75) | 1 |
|  |  |  |  | 40 | VDGQDSQPL (SEQ ID NO:76) | 40 | 40 | VDKQDAQPL (SEQ ID NO:122) | 40 |
|  | 80 | EDLLMGTLGI (SEQ ID NO:38) | 40 | 80 | QQLLLGTLNI (SEQ ID NO:91) | 1 | 80 | QDLLLGTLNI (SEQ ID NO:131) | 40 |
| B_3801 | 78 | TLEDLLLMGTL (SEQ ID NO:39) | 8 | 78 | EVQQLLLGTL (SEQ ID NO:92) | 1 | 79 | LQDLLLGTL (SEQ ID NO:120) | 4 |

TABLE 4-continued

| HLA Type | HPV Type 16 | | | HPV Type 6 | | | HPV Type 11 | | |
|---|---|---|---|---|---|---|---|---|---|
| | start | sequence | $T_{1/2}$ | start | sequence | $T_{1/2}$ | start | sequence | $T_{1/2}$ |
| | 50 | AHYNIVTFC (SEQ ID NO:40) | 4 | 50 | QHYQIVTCC (SEQ ID NO:93) | 4 | 50 | QHYQILTCC (SEQ ID NO:132) | 3 |
| | 5 | TPTLHEYML (SEQ ID NO:7) | 2 | 4 | RHVTLKDIVL (SEQ ID NO:94) | 30 | 4 | RLVTLKDIVL (SEQ ID NO:113) | 1 |
| | | | | 39 | EVDGQDSQPL (SEQ ID NO:61) | 6 | 39 | KVDKQDAQPL (SEQ ID NO:114) | 3 |
| | 71 | STHVDIRTL (SEQ ID NO:41) | 1 | 71 | CTETDIREV (SEQ ID NO:95) | 1 | 71 | CTDGDIRQL (SEQ ID NO:133) | 6 |
| B_3901 | 78 | TLEDLLMGTL (SEQ ID NO:42) | 27 | 79 | EVQQLLLGTL (SEQ ID NO:56) | 5 | 79 | LQDLLLGTL (SEQ ID NO:120) | 14 |
| | 73 | HVDIRTLEDL (SEQ ID NO:43) | 14 | 73 | ETDIREVQQL (SEQ ID NO:96) | 14 | 74 | GDIRQLQDL (SEQ ID NO:119) | 1 |
| | 77 | RTLEDLLMGT (SEQ ID NO:18) | 1 | 76 | IREVQQLLL (SEQ ID NO:70) | 45 | 75 | DIRQLQDLL (SEQ ID NO:126) | 1 |
| | 4 | DTPTLHEYML (SEQ ID NO:11) | 2 | 4 | RHVTLKDIVL (SEQ ID NO:94) | 90 | 3 | GRLVTLKDI (SEQ ID NO:116) | 15 |
| B_3902 | 59 | CKCDSTLRL (SEQ ID NO:44) | 20 | 59 | CGCDSNVRL (SEQ ID NO:97) | 2 | 59 | CGCDSNVRLV (SEQ ID NO:97) | 3 |
| | 7 | TLHEYMLDL (SEQ ID NO:4) | 2 | 7 | TLKDIVLDL (SEQ ID NO:53) | 1 | 6 | VTLKDIVLDL (SEQ ID NO:53) | 9 |
| | 79 | LEDLLMGTL (SEQ ID NO:22) | 1 | 79 | VQQLLLGTL (SEQ ID NO:56) | 24 | 79 | LQLQDLLLGTL (SEQ ID NO:134) | 24 |
| | 15 | LQPETTDLY (SEQ ID NO:26) | 1 | 15 | LQPPDVGL (SEQ ID NO:98) | 20 | 15 | LQPPDPVGL (SEQ ID NO:80) | 20 |
| B_4403 | 36 | DEIDGPAGQA (SEQ ID NO:19) | 90 | 35 | DEVDEVDGQ (SEQ ID NO:71) | 7 | 35 | DEVDKVDKQ (SEQ ID NO:118) | 16 |
| | 3 | GDTPTLHEY (SEQ ID NO:45) | 45 | | | | | | |
| | 44 | QAEPDRAHY (SEQ ID NO:1) | 6 | 44 | DSQPLKQHY (SEQ ID NO:51) | 18 | 44 | DAQPLTQHY (SEQ ID NO:106) | 27 |
| | | | | 77 | REVQQLLLGT (SEQ ID NO:73) | 12 | | | |
| B_5101 | 46 | EPDRAHYNI (SEQ ID NO:29) | 880 | 46 | QPLKQHYQI (SEQ ID NO:83) | 440 | 46 | QPLTQHYQI (SEQ ID NO:135) | 400 |
| | 84 | MGTLGIVCPI (SEQ ID NO:46) | 114 | 84 | LGTLNIVCPI (SEQ ID NO:99) | 114 | 84 | LGTLNIVCPI (SEQ ID NO:99) | 114 |
| B_5102 | 46 | EPDRAHYNI (SEQ ID NO:29) | 220 | 46 | QPLKQHYQI (SEQ ID NO:83) | 1452 | 46 | QPLTQHYQI (SEQ ID NO:135) | 1452 |
| | 84 | MGTLGIVCPI (SEQ ID NO:46) | 88 | 84 | LGTLNIVCPI (SEQ ID NO:99) | 88 | 84 | LGTLNIVCPI (SEQ ID NO:99) | 88 |
| | | | | 21 | VGLHCYEQLV (SEQ ID NO:90) | 145 | 21 | VGLHCYEQL (SEQ ID NO:75) | 73 |
| B_5103 | 46 | EPDRAHYNI (SEQ ID NO:29 | 58 | 46 | QPLKQHYQI (SEQ ID NO:83) | 83 | 46 | QPLTQHYQI (SEQ ID NO:135) | 58 |
| | 84 | MGTLGIVCPI (SEQ ID NO:46) | 44 | 84 | LGTLNIVCPI (SEQ ID NO:99) | 44 | 84 | LGTLNIVCPI (SEQ ID NO:99) | 44 |

TABLE 4-continued

| HLA Type | HPV Type 16 | | | HPV Type 6 | | | HPV Type 11 | | |
|---|---|---|---|---|---|---|---|---|---|
| | start | sequence | $T_{1/2}$ | start | sequence | $T_{1/2}$ | start | sequence | $T_{1/2}$ |
| | | | | 21 | VGLHCYEQLVL (SEQ ID NO:90) | 53 | | | |
| B_5201 | 46 | EPDRAHYNIV (SEQ ID NO:36) | 100 | 46 | QPLKQHYQIV (SEQ ID NO:100) | 132 | 46 | QPLTQHYQIL (SEQ ID NO:127) | 22 |
| | 81 | DLLMGTLGIV (SEQ ID NO:47) | 33 | 82 | LLLGTLNIV (SEQ ID NO:54) | 50 | 82 | LLLGTLNIV (SEQ ID NO:54) | 50 |
| | | | | 60 | GCDSNVRLVV (SEQ ID NO:101) | 40 | 60 | GCDSNVRLVV (SEQ ID NO:101) | 40 |
| B_5801 | 49 | RAHYNIVTF (SEQ ID NO:48) | 79.0 | 49 | KQHYQIVTCC (SEQ ID NO:102) | 0 | 48.0 | LTQHYQILTC (SEQ ID NO:136) | 3.0 |
| | 77 | RTLEDLLMGT (SEQ ID NO:18) | 24.0 | 77 | REVQQLLLGT (SEQ ID NO:73) | 0 | 77.0 | RQLQDLLLGT (SEQ ID NO:137) | 0.1 |
| | 6 | PTLHEYMLDL (SEQ ID NO:49) | 0.2 | 6 | VTLKDIVLDL (SEQ ID NO:69) | 8 | 6.0 | VTLKDIVLDL (SEQ ID NO:69) | 8.0 |
| | 44 | QAEPDRAHY (SEQ ID NO:1) | 6.0 | 44 | DSQPLKQHY (SEQ ID NO:51) | 5 | 44.0 | DAQPLTQHY (SEQ ID NO:106) | 3.0 |
| | 85 | GTLGIVCPI (SEQ ID NO:50) | 4.0 | 85 | GTLNIVCPI (SEQ ID NO:103) | 4 | 85.0 | GTLNIVCPI (SEQ ID NO:103) | 4.0 |
| Cw_0301 | 20 | TDLYCYEQL (SEQ ID NO:23) | 100 | 21 | VGLHCYEQL (SEQ ID NO:75) | 100 | 21 | VGLHCYEQL (SEQ ID NO:75) | 100 |
| | 74 | VDIRTLEDL (SEQ ID NO:20) | 30 | 74 | TDIREVQQL (SEQ ID NO:72) | 36 | 74 | GDIRQLQDL (SEQ ID NO:119) | 36 |
| | | | | 46 | QPLKQHYQIV (SEQ ID NO:100) | 6 | 46 | QPLTQHYQIL (SEQ ID NO:127) | 120 |
| Cw_0401 | 56 | TFCCKCDSTL (SEQ ID NO:8) | 200 | | | | 57 | CCCGCDSNV (SEQ ID NO:138) | 1 |
| | 5 | TPTLHEYML (SEQ ID NO:7) | 88 | | | | | | |
| | 73 | HVDIRTLEDL (SEQ ID NO:43) | 14 | 73 | ETDIREVQQL (SEQ ID NO:96) | 12 | 73 | DGDIRQLQDL (SEQ ID NO:139) | 12 |
| | 46 | EPDRAHYNI (SEQ ID NO:29) | 17 | 46 | QPLKQHYQIV (SEQ ID NO:100) | 11 | 46 | QPLTQHYQIL (SEQ ID NO:127) | 88 |
| Cw_0602 | 79 | LEDLLMGTL (SEQ ID NO:22) | 6 | 79 | VQQLLLGTL (SEQ ID NO:56) | 13 | 79 | LQDLLLGTL (SEQ ID NO:120) | 13 |
| | 85 | GTLGIVCPI (SEQ ID NO:50) | 6 | 85 | GTLNIVCPI (SEQ ID NO:103) | 6 | 85 | GTLNIVCPI (SEQ ID NO:103) | 6 |
| | 7 | TLHEYMLDL (SEQ ID NO:4) | 2 | 7 | TLKDIVLDL (SEQ ID NO:53) | 12 | 7 | TLKDIVLDL (SEQ ID NO:53) | 121 |
| Cw_0702 | 3 | GDTPTLHEY (SEQ ID NO:45) | 27 | 3 | GRHVTLKDI (SEQ ID NO:68) | 1 | 3 | GRLVTLKDI (SEQ ID NO:116) | 1 |
| | 15 | LQPETTDLY (SEQ ID NO:26) | 8 | 16 | QPPDPVGLHC (SEQ ID NO:104) | 3 | 16 | QPPDPVGLHC (SEQ ID NO:104) | 3 |
| | 43 | GQAEPDRAHY (SEQ ID NO:27) | 2 | 43 | QDSQPLKQHY (SEQ ID NO:105) | 11 | 43 | QDAQPLTQHY (SEQ ID NO:140) | 32 |

TABLE 4-continued

| HLA Type | HPV Type 16 | | | HPV Type 6 | | | HPV Type 11 | | |
|---|---|---|---|---|---|---|---|---|---|
| | start | sequence | $T_{1/2}$ | start | sequence | $T_{1/2}$ | start | sequence | $T_{1/2}$ |
| | 7 | TLHEYMLDL (SEQ ID NO:4) | 1 | 7 | TLKDIVLDL (SEQ ID NO:53) | 4 | 7 | TLKDIVLDL (SEQ ID NO:53) | 4 |

The peptide sequences in bold indicate the top two binders for each HLA molecule, and for each the E7 protein from each HPV type.

The results in Table 4 suggest that, depending on the specific HLA molecule examined, the HPV type 16 E7 antigen may trigger a cell mediated immune response against the E7 antigen of other HPV types. For example, for HLA B 2705, a high level of binding was predicted for peptides starting from amino acid position 76 of E7 for all three HPV types. Thus, it is possible that, for patients expressing this HLA molecule, an HPV type 16 E7 composition would be cross-reactive and useful for treating or preventing infection by HPV types 6 and 11. Each of the bolded peptide fragments in Table 4 represents a possible antigenic fragment that can be included in the compositions (e.g., the fusion polypeptides described herein), as a substitute for the complete E7 viral antigen. Of course, two or more such putative HLA epitopes, or a long fragment containing many putative HLA epitopes, can also be used.

What is claimed is:

1. A method of treating anal cancer or anal dysplasia, in a subject, the method comprising administering to the subject a composition comprising a therapeutically effective amount of a fusion protein comprising (1) a Hsp60 protein, or an immunostimulatory fragment thereof, and (2) a human papillomavirus (HPV) type 16 E7 protein, wherein the subject is infected with an HPV of type 5, 6, 11, 18, 31, 33, 35, 45, 54, 60, or 70.

2. The method of claim 1, wherein the Hsp60 protein is a mycobacterial Hsp60 protein.

3. The method of claim 2, wherein the mycobacterial Hsp60 protein is a *Mycobacterium bovis* Hsp60 protein.

4. The method of claim 3, wherein the mycobacterial Hsp60 protein is a *Mycobacterium bovis* BCG Hsp65 protein.

5. The method of claim 1, wherein the composition contains about 50 to 5000 µg of the fusion protein.

6. The method of claim 5, wherein the composition contains about 100 to 2000 µg of the fusion protein.

7. The method of claim 1, wherein the composition is free of adjuvant.

8. The method of claim 1, wherein the subject is a mammal.

9. The method of claim 8, wherein the mammal is a human.

10. The method of claim 1, wherein the subject is not identified as being infected with the type of HPV that is administered prior to administration of the composition.

11. A method of treating anal cancer or anal dysplasia in a subject, the method comprising identifying a subject having, or suspected of having, anal cancer or anal dysplasia associated with a human papillomavirus (HPV) of type 5, 6, 11, 18, 31, 33, 35, 45, 54, 60, or 70; administering to the subject a nucleic acid encoding a fusion polypeptide comprising (1) a Hsp60 protein, or an imnmunostimulatory fragment thereof and (2) a HPV type 16 E7 protein; and expressing the fusion polypeptide in the subject in an amount sufficient to treat the anal cancer or anal dysplasia.

12. The method of claim 11, wherein the nucleic acid is contained within a viral vector.

13. The method of claim 11, wherein the subject has a disease or condition associated with an HPV of type 6, 11, 33, 45 or 70.

14. The method of claim 11, wherein the subject has a disease or condition associated with an HPV of type 6 or 11.

15. The method of claim 11, wherein the subject has anal cancer or anal dysplasia associated with HPV type 6 infection.

16. The method of claim 11, wherein the subject has anal cancer or anal dysplasia associated with HPV type 11 infection.

17. The method of claim 11, wherein the Hsp60 protein is a mycobacterial Hsp60 protein.

18. The method of claim 17, wherein the mycobacterial Hsp60 protein is a *Mycobacterium bovis* Hsp60 protein.

19. The method of claim 18, wherein the mycobacterial Hsp60 protein is a *Mycobacterium bovis* BCG Hsp65.

20. The method of claim 11, wherein the composition contains about 50 to 5000 µg of the fusion protein.

21. The method of claim 20, wherein the composition contains about 100 to 2000 µg of the fusion protein.

22. The method of claim 11, wherein the composition is free of adjuvant.

23. The method of claim 11, wherein the subject is a mammal.

24. The method of claim 23, wherein the mammal is a human.

25. The method of claim 11, wherein the subject is not identified as being infected with the type of HPV that is administered prior to administration of the composition.

* * * * *